United States Patent
Kane et al.

(10) Patent No.: US 10,933,245 B2
(45) Date of Patent: *Mar. 2, 2021

(54) CONDUCTED COMMUNICATION IN A MEDICAL DEVICE SYSTEM

(71) Applicant: CARDIAC PACEMAKERS, INC., St. Paul, MN (US)

(72) Inventors: Michael J. Kane, St. Paul, MN (US); Brian L. Schmidt, White Bear Lake, MN (US); Brendan Early Koop, Ham Lake, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 196 days.

This patent is subject to a terminal disclaimer.

(21) Appl. No.: 16/213,762

(22) Filed: Dec. 7, 2018

(65) Prior Publication Data

US 2019/0105502 A1 Apr. 11, 2019

Related U.S. Application Data

(63) Continuation of application No. 15/381,837, filed on Dec. 16, 2016, now Pat. No. 10,183,170.

(Continued)

(51) Int. Cl.
*A61N 1/372* (2006.01)
*A61N 1/375* (2006.01)

(52) U.S. Cl.
CPC ..... *A61N 1/37217* (2013.01); *A61N 1/37288* (2013.01); *A61N 1/3756* (2013.01)

(58) Field of Classification Search
CPC ............ A61N 1/37217; A61N 1/37288; A61N 1/3756

See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318 B2, 11/2014, Jacobson et al. (withdrawn)

(Continued)

*Primary Examiner* — Catherine M Voorhees
(74) *Attorney, Agent, or Firm* — Seager, Tufte & Wickhem LLP

(57) ABSTRACT

An implantable medical device for implantation into a patient may include a housing, a pulse generation circuit disposed at least partially within the housing, a plurality of electrodes electrically coupled to the pulse generation circuit, the plurality of electrodes being exposed external to the housing, and a controller operatively coupled to the pulse generation circuit. The controller may be configured to command the pulse generation circuit to deliver a phasic conducted communication pulse via at least two of the plurality of electrodes. Additionally, the phasic conducted communication pulse may comprise a first phase having a first polarity followed by a second phase having an opposite second polarity, wherein the second phase may have a duration of less than 60 microseconds, and wherein the first phase having may have a duration of between five percent and eighty percent of the duration of the second phase.

20 Claims, 12 Drawing Sheets

Related U.S. Application Data

(60) Provisional application No. 62/268,751, filed on Dec. 17, 2015.

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | Decoriolis et al. |
| 5,370,667 A | 12/1994 | Alt |
| 5,372,606 A | 12/1994 | Lang et al. |
| 5,376,106 A | 12/1994 | Stahmann et al. |
| 5,383,912 A | 1/1995 | Cox et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras et al. |
| 5,944,744 A | 8/1999 | Paul et al. |
| 5,954,757 A | 9/1999 | Gray |
| 5,978,713 A | 11/1999 | Prutchi et al. |
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |

(56) References Cited

U.S. PATENT DOCUMENTS

| | | |
|---|---|---|
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B1 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,024,241 B1 | 4/2006 | Bornzin et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |

(56) References Cited

U.S. PATENT DOCUMENTS

| | | |
|---|---|---|
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,493,174 B2 | 2/2009 | Belalcazar et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |

(56) References Cited

U.S. PATENT DOCUMENTS

| | | |
|---|---|---|
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,255,048 B2 | 8/2012 | Dal Molin et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,625,661 B2 | 1/2014 | Lee et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |

(56) References Cited

U.S. PATENT DOCUMENTS

| | | |
|---|---|---|
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 10,183,170 B2 * | 1/2019 | Kane ............... A61N 1/37288 |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 * | 7/2002 | Berg ............... A61N 1/3727 607/60 |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |

(56) References Cited

U.S. PATENT DOCUMENTS

| | | |
|---|---|---|
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0173493 A1 | 8/2006 | Armstrong et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0053470 A1 | 3/2012 | Wong et al. |

(56) References Cited

U.S. PATENT DOCUMENTS

| | | |
|---|---|---|
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172060 A1 | 6/2014 | Bomzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0309706 A1 | 10/2014 | Jacobson |
| 2014/0379041 A1 | 12/2014 | Foster |
| 2014/0379048 A1* | 12/2014 | Von Arx ............ A61N 1/37288 607/60 |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |

(56) References Cited

U.S. PATENT DOCUMENTS

| | | |
|---|---|---|
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |
| 2015/0328459 A1 | 11/2015 | Chin et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0121127 A1 | 5/2016 | Klimovitch et al. |
| 2016/0121128 A1 | 5/2016 | Fishier et al. |
| 2016/0121129 A1 | 5/2016 | Persson et al. |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0035315 A1 | 2/2017 | Jackson |
| 2017/0043173 A1 | 2/2017 | Sharma et al. |
| 2017/0043174 A1 | 2/2017 | Greenhut et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |
| WO | 2010013170 A1 | 2/2010 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |

OTHER PUBLICATIONS

International Search Report and Written Opinion dated Jun. 9, 2017 for International Application No. PCT/US2016/067248.

"Instructions for Use System 1, Leadless Cardiac Pacemaker (LCP) and Delivery Catheter," Nanostim Leadless Pacemakers, pp. 1-28, 2013.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Notification of Transmittal of the International Search Report and the Written Opinion of the International Searching Authority, or the Declaration, dated Jan. 29, 2016, 15 pages.

Seyedi et al., "A Survey on Intrabody Communications for Body Area Network Application," IEEE Transactions on Biomedical Engineering, vol. 60(8): 2067-2079, 2013.

Spickler et al., "Totally Self-Contained Intracardiac Pacemaker," Journal of Electrocardiology, vol. 3(384): 324-331, 1970.

Wegmüller, "Intra-Body Communication for Biomedical Sensor Networks," Diss. ETH, No. 17323, 1-173, 2007.

* cited by examiner

CONDUCTED COMMUNICATION IN A MEDICAL DEVICE SYSTEM

CROSS REFERENCE TO RELATED APPLICATIONS

This application is a continuation of co-pending U.S. patent application Ser. No. 15/381,837, filed Dec. 16, 2016, which claims the benefit of U.S. Provisional Patent Application Ser. No. 62/268,751 filed on Dec. 17, 2015, both of which are incorporated herein by reference.

TECHNICAL FIELD

The present disclosure generally relates to medical devices, and more particularly to conducted communications between medical devices in a multi-device system.

BACKGROUND

Implantable medical devices are commonly used to monitor, diagnose and/or treat various conditions in the body. Such devices can include, for example, neuro-stimulators, diagnostic devices, chemical sensors, pressure sensors, temperature sensors, etc. Pacing devices are another example. Pacing devices are used to treat patients suffering from various heart conditions. Many heart conditions can lead to rapid, irregular, and/or inefficient heart contractions. To help alleviate some of these heart conditions, various cardiac stimulating/sensor devices (e.g., pacemakers, defibrillators, etc.) are often implanted into a patient's body. Such devices are then used to monitor and provide electrical stimulation to the heart to help the heart operate in a more normal, efficient and/or safe manner.

Regardless of the type of implantable device, it is often desirable to establish communication with the implanted device. In some cases, conducted communication is used, which relies on electrical communication signals or pulses that "conducted" through the body. In some cases, such electrical communication signals or pulses can undesirably stimulated body tissue. What would be desirable is an improved conducted communication scheme that is less likely to stimulate body tissue.

SUMMARY

The present disclosure generally relates to systems, devices, and methods for communicating with or between implantable medical devices. In a first illustrative embodiment, an implantable medical device for implantation into a patient may comprise a housing, a pulse generation circuit disposed at least partially within the housing, a plurality of electrodes electrically coupled to the pulse generation circuit, the plurality of electrodes being exposed external to the housing, and a controller operatively coupled to the pulse generation circuit. In some instances, the controller may be configured to command the pulse generation circuit to deliver a phasic conducted communication pulse via at least two of the plurality of electrodes. The phasic conducted communication pulse may comprise a first phase having a first polarity followed by a second phase having an opposite second polarity. The second phase may have a duration of less than 60 microseconds. In some cases, the first phase may have a duration of between five percent and eighty percent of the duration of the second phase.

Additionally, or alternatively, the first phase may have a first phase amplitude, where the absolute value of the first phase amplitude may be between 1 and 15 volts.

Additionally, or alternatively, in any of the above embodiments with respect to the first illustrative embodiment, the second phase may have a second phase amplitude, where the absolute value of the second phase amplitude may be between 1 and 15 volts.

Additionally, or alternatively, in any of the above embodiments with respect to the first illustrative embodiment, the first phase may have a first phase amplitude with an absolute value of between 2 and 7 volts, and the second phase may have a second phase amplitude with an absolute value of between 2 and 7 volts.

Additionally, or alternatively, in any of the above embodiments with respect to the first illustrative embodiment, the first phase may have a first phase amplitude with an absolute value of between 1 and 4 volts, and the second phase may have a second phase amplitude with an absolute value of between 1 and 4 volts.

Additionally, or alternatively, in any of the above embodiments with respect to the first illustrative embodiment, the second phase may have a duration of less than 60 microseconds.

Additionally, or alternatively, in any of the above embodiments with respect to the first illustrative embodiment, the second phase may have a duration of less than 30 microseconds.

Additionally, or alternatively, in any of the above embodiments with respect to the first illustrative embodiment, the second phase may have a duration of less than 20 microseconds.

Additionally, or alternatively, in any of the above embodiments with respect to the first illustrative embodiment, the first phase may have a duration of between forty percent and sixty percent of the duration of the second phase.

Additionally, or alternatively, in any of the above embodiments with respect to the first illustrative embodiment, the first phase and the second phase may each be a substantially rectangular pulse.

Additionally, or alternatively, in any of the above embodiments with respect to the first illustrative embodiment, the first phase and the second phase may each be substantially a rectangular pulse, a saw tooth pulse, an exponential pulse, a trapezoid pulse, or a stepped pulse.

Additionally, or alternatively, in any of the above embodiments with respect to the first illustrative embodiment, the phasic conducted communication pulse may comprise a third phase.

Additionally, or alternatively, in any of the above embodiments with respect to the first illustrative embodiment, the third phase may have the first polarity.

Additionally, or alternatively, in any of the above embodiments with respect to the first illustrative embodiment, the phasic conducted communication pulse may be substantially charge balanced.

Additionally, or alternatively, in any of the above embodiments with respect to the first illustrative embodiment, the phasic conducted communication pulse may have four or more phases.

In a second illustrative embodiment, a medical device may comprise a housing, a pulse generation circuit disposed at least partially within the housing, a plurality of electrodes electrically coupled to the pulse generation circuit, the plurality of electrodes being exposed externally to the housing, and a controller operatively coupled to the pulse generation circuit. In some instances, the controller may be configured to command the pulse generation circuit to deliver a phasic conducted communication pulse via at least two of the plurality of electrodes. Additionally, in some cases, the phasic conducted communication pulse may comprise at least three phases.

Additionally, or alternatively, with respect to the second illustrative embodiment, the phasic conducted communication pulse may comprise a first phase, a second phase, and a third phase, with each phase having a duration and an amplitude, and wherein the first phase and the third phase may have a first polarity and the second phase may have a second opposite polarity.

Additionally, or alternatively, in any of the above embodiments with respect to the second illustrative embodiment, the duration of the second phase may be less than 60 microseconds.

Additionally, or alternatively, in any of the above embodiments with respect to the second illustrative embodiment, the duration of the first phase of the phasic conducted communication pulse may be between five percent and eighty percent of the duration of the second phase of the phasic conducted communication pulse.

Additionally, or alternatively, in any of the above embodiments with respect to the second illustrative embodiment, the duration of the second phase may be less than 50 microseconds, and the duration of the first phase may be between forty percent and sixty percent of the duration of the second phase.

Additionally, or alternatively, in any of the above embodiments with respect to the second illustrative embodiment, the phasic conducted communication pulse may be substantially charge balanced.

Additionally, or alternatively, in any of the above embodiments with respect to the second illustrative embodiment, the phasic conducted communication pulse may have four or more phases, each of the four or more phases having a duration.

In a third illustrative embodiment, a medical device may comprise a housing, a plurality of electrodes coupled to the housing, and a communication circuit electrically connected to the plurality of electrodes. In at least some instances, the communication circuit may be configured to deliver a phasic conducted communication pulse via two or more of the plurality of electrodes for communicating information external to the medical device. In at least some cases, the phasic conducted communication pulse may comprises a first phase, followed by a second phase, followed by a third phase, where the first phase and the third phase have a first polarity, and the second phase has an opposite second polarity.

Additionally, or alternatively, with respect to the third illustrative embodiment, the second phase may have a duration of less than 60 microseconds, and the first phase may have a duration of between five percent and eighty percent of the duration of the second phase.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
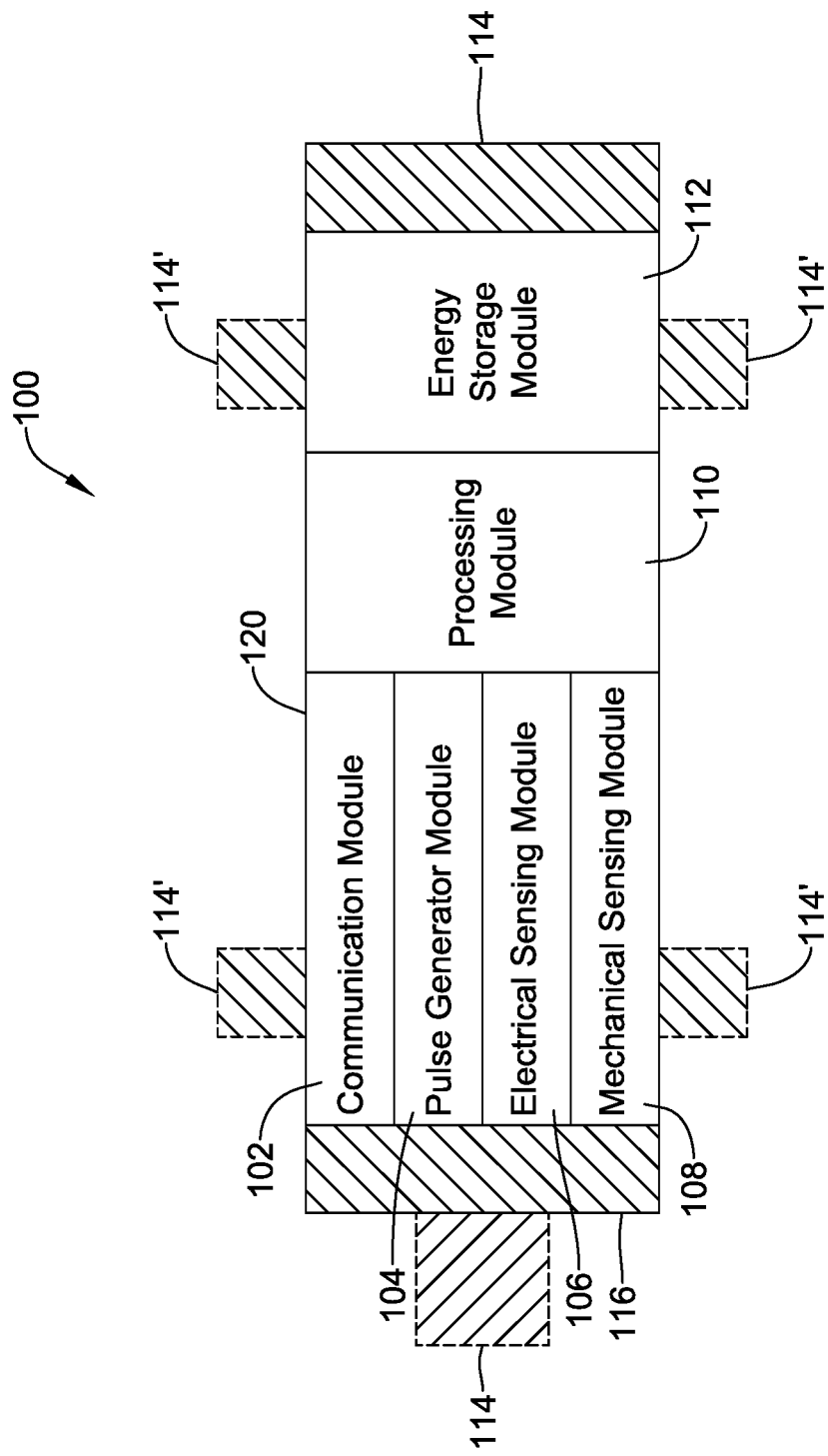
FIG. 1 is a schematic block diagram of an illustrative leadless cardiac pacemaker (LCP) according to one example embodiment of the present disclosure.

While the disclosure is amenable to various modifications and alternative forms, specifics thereof have been shown by way of embodiment in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

The present disclosure relates to systems, devices, and methods for communicating with or between implantable medical devices such as heart stimulating devices, neurostimulators, diagnostic devices, chemical sensors, pressure sensors, temperature sensors, etc. Merely for convenience, many of the examples described herein are directed at heart stimulating devices such as implantable pacemakers and/or implantable cardioverter-defibrillators. The intention is not to limit the disclosure to implantable pacemakers and/or implantable cardioverter-defibrillators. Rather, the intention is to cover communication with or between any suitable implantable medical device.

FIG. 1 is a conceptual schematic block diagram of an illustrative leadless cardiac pacemaker (LCP) that may be implanted on the heart or within a chamber of the heart and may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 1, LCP 100 may be a compact device with all components housed within LCP 100 or directly on housing 120. In some instances, LCP 100 may include communication module 102, pulse generator module 104, electrical sensing module 106, mechanical sensing module 108, processing module 110, energy storage module 112, and electrodes 114.

As depicted in FIG. 1, LCP 100 may include electrodes 114, which can be secured relative to housing 120 and electrically exposed to tissue and/or blood surrounding LCP 100.

Electrodes 114 may generally conduct electrical signals to and from LCP 100 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG).

Electrodes 114 may include one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In embodiments where electrodes 114 are secured directly to housing 120, an insulative material may electrically isolate the electrodes 114 from adjacent electrodes, housing 120, and/or other parts of LCP 100. In some instances, some or all of electrodes 114 may be spaced from housing 120 and connected to housing 120 and/or other components of LCP 100 through connecting wires. In such instances, the electrodes 114 may be placed on a tail (not shown) that extends out away from the housing 120. As shown in FIG. 1, in some embodiments, LCP 100 may include electrodes 114'. Electrodes 114' may be in addition to electrodes 114, or may replace one or more of electrodes 114. Electrodes 114' may be similar to electrodes 114 except that electrodes 114' are disposed on the sides of LCP 100. In some cases, electrodes 114' may increase the number of electrodes by which LCP 100 may deliver communication signals and/or electrical stimulation pulses, and/or may sense intrinsic cardiac electrical signals, communication signals, and/or electrical stimulation pulses.

Electrodes 114 and/or 114' may assume any of a variety of sizes and/or shapes, and may be spaced at any of a variety of spacings. For example, electrodes 114 may have an outer diameter of two to twenty millimeters (mm). In other embodiments, electrodes 114 and/or 114' may have a diameter of two, three, five, seven millimeters (mm), or any other suitable diameter, dimension and/or shape. Example lengths for electrodes 114 and/or 114' may include, for example, one, three, five, ten millimeters (mm), or any other suitable length. As used herein, the length is a dimension of electrodes 114 and/or 114' that extends away from the outer surface of the housing 120. In some instances, at least some of electrodes 114 and/or 114' may be spaced from one another by a distance of twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In the embodiment shown, communication module 102 may be electrically coupled to electrodes 114 and/or 114' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. Communication module 102 may additionally be configured to sense for communication signals delivered by other devices, which may be located external or internal to the patient's body.

Communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, LCP 100 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, accelerometer signals, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

In at least some embodiments, communication module 102 (or LCP 100) may further include switching circuitry to selectively connect one or more of electrodes 114 and/or 114' to communication module 102 in order to select which electrodes 114 and/or 114' that communication module 102 delivers communication pulses. It is contemplated that communication module 102 may be communicating with other devices via conducted signals, radio frequency (RF) signals, optical signals, acoustic signals, inductive coupling, and/or any other suitable communication methodology. Where communication module 102 generates electrical communication signals, communication module 102 may include one or more capacitor elements and/or other charge storage devices to aid in generating and delivering communication signals. In the embodiment shown, communication module 102 may use energy stored in energy storage module 112 to generate the communication signals. In at least some examples, communication module 102 may include a switching circuit that is connected to energy storage module 112 and, with the switching circuitry, may connect energy storage module 112 to one or more of electrodes 114/114' to generate the communication signals.

As shown in FIG. 1, a pulse generator module 104 may be electrically connected to one or more of electrodes 114 and/or 114'. Pulse generator module 104 may be configured to generate electrical stimulation pulses and deliver the electrical stimulation pulses to tissues of a patient via one or more of the electrodes 114 and/or 114' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 104 may generate electrical stimulation pacing pulses for capturing the heart of the patient, i.e. causing the heart to contract in response to the delivered electrical stimulation pulse. In some of these cases, LCP 100 may vary the rate at which pulse generator module 104 generates the electrical stimulation pulses, for example in rate adaptive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. When used to treat other ailments, the pulse generator module 104 may generate electrical stimulation pulses suitable for neurostimulation therapy or the like. Pulse generator module 104 may include one or more capacitor elements and/or other charge storage devices to aid in generating and delivering appropriate electrical stimulation pulses. In at least some embodiments, pulse generator module 104 may use energy stored in energy storage module 112 to generate the electrical stimulation pulses. In some particular embodiments, pulse generator module 104 may include a switching circuit that is connected to energy storage module 112 and may connect energy storage module 112 to one or more of electrodes 114/114' to generate electrical stimulation pulses.

LCP 100 may further include an electrical sensing module 106 and mechanical sensing module 108. Electrical sensing module 106 may be configured to sense intrinsic cardiac electrical signals conducted from electrodes 114 and/or 114' to electrical sensing module 106.

For example, electrical sensing module 106 may be electrically connected to one or more electrodes 114 and/or 114' and electrical sensing module 106 may be configured to receive cardiac electrical signals conducted through electrodes 114 and/or 114' via a sensor amplifier or the like. In some embodiments, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. Mechanical sensing module 108 may include, or be electrically connected to, various sensors, such as accelerometers, including multi-axis accelerometers such as two- or three-axis accelerometers, gyroscopes, including multi-axis gyroscopes such as two- or three-axis gyroscopes, blood pressure sensors, heart sound sensors, piezoelectric sensors, blood-oxygen sensors, and/or other sensors which measure one or more physiological parameters of the heart and/or patient. Mechanical sensing module 108, when present, may gather signals from the sensors indicative of the various physiological parameters. Both electrical sensing module 106 and mechanical sensing module 108 may be connected to processing module 110 and may provide signals representative of the sensed cardiac electrical signals and/or physiological signals to processing module 110. Although described with respect to FIG. 1 as separate sensing modules, in some embodiments, electrical sensing module 106 and mechanical sensing module 108 may be combined into a single module. In at least some examples, LCP 100 may only include one of electrical sensing module 106 and mechanical sensing module 108. In some cases, any combination of the processing module 110, electrical sensing module 106, mechanical sensing module 108, communication module 102, pulse generator module 104 and/or energy storage module may be considered a controller of the LCP 100.

Processing module 110 may be configured to direct the operation of LCP 100 and may, in some embodiments, be termed a controller. For example, processing module 110 may be configured to receive cardiac electrical signals from electrical sensing module 106 and/or physiological signals from mechanical sensing module 108. Based on the received signals, processing module 110 may determine, for example, occurrences and types of arrhythmias and other determinations such as whether LCP 100 has become dislodged. Processing module 110 may further receive information from communication module 102. In some embodiments, processing module 110 may additionally use such received information to determine occurrences and types of arrhythmias and/or and other determinations such as whether LCP 100 has become dislodged. In still some additional embodiments, LCP 100 may use the received information instead of the signals received from electrical sensing module 106 and/or mechanical sensing module 108—for instance if the received information is deemed to be more accurate than the signals received from electrical sensing module 106 and/or mechanical sensing module 108 or if electrical sensing module 106 and/or mechanical sensing module 108 have been disabled or omitted from LCP 100.

After determining an occurrence of an arrhythmia, processing module 110 may control pulse generator module 104 to generate electrical stimulation pulses in accordance with one or more electrical stimulation therapies to treat the determined arrhythmia. For example, processing module 110 may control pulse generator module 104 to generate pacing pulses with varying parameters and in different sequences to effectuate one or more electrical stimulation therapies. As one example, in controlling pulse generator module 104 to deliver bradycardia pacing therapy, processing module 110 may control pulse generator module 104 to deliver pacing pulses designed to capture the heart of the patient at a regular interval to help prevent the heart of a patient from falling below a predetermined threshold. In some cases, the rate of pacing may be increased with an increased activity level of the patient (e.g. rate adaptive pacing). For instance, processing module 110 may monitor one or more physiological parameters of the patient which may indicate a need for an increased heart rate (e.g. due to increased metabolic demand). Processing module 110 may then increase the rate at which pulse generator module 104 generates electrical stimulation pulses. Adjusting the rate of delivery of the electrical stimulation pulses based on the one or more physiological parameters may extend the battery life of LCP 100 by only requiring higher rates of delivery of electrical stimulation pulses when the physiological parameters indicate there is a need for increased cardiac output.

Additionally, adjusting the rate of delivery of the electrical stimulation pulses may increase a comfort level of the patient by more closely matching the rate of delivery of electrical stimulation pulses with the cardiac output need of the patient.

For ATP therapy, processing module 110 may control pulse generator module 104 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, processing module 110 may control pulse generator module 104 to reduce the rate of delivered pacing pulses down to a safer level. In CRT, processing module 110 may control pulse generator module 104 to deliver pacing pulses in coordination with another device to cause the heart to contract more efficiently. In cases where pulse generator module 104 is capable of generating defibrillation and/or cardioversion pulses for defibrillation/cardioversion therapy, processing module 110 may control pulse generator module 104 to generate such defibrillation and/or cardioversion pulses. In some cases, processing module 110 may control pulse generator module 104 to generate electrical stimulation pulses to provide electrical stimulation therapies different than those examples described above.

Aside from controlling pulse generator module 104 to generate different types of electrical stimulation pulses and in different sequences, in some embodiments, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart. Such control of the specific parameters of the various electrical stimulation pulses may help LCP 100 provide more effective delivery of electrical stimulation therapy.

In some embodiments, processing module 110 may further control communication module 102 to send information to other devices. For example, processing module 110 may control communication module 102 to generate one or more communication signals for communicating with other devices of a system of devices. For instance, processing module 110 may control communication module 102 to generate communication signals in particular pulse sequences, where the specific sequences convey different information. Communication module 102 may also receive communication signals for potential action by processing module 110.

In further embodiments, processing module 110 may control switching circuitry by which communication module 102 and pulse generator module 104 deliver communication signals and/or electrical stimulation pulses to tissue of the patient. As described above, both communication module 102 and pulse generator module 104 may include circuitry for connecting one or more electrodes 114 and/or 114' to communication module 102 and/or pulse generator module 104 so those modules may deliver the communication signals and electrical stimulation pulses to tissue of the patient. The specific combination of one or more electrodes by which communication module 102 and/or pulse generator module 104 deliver communication signals and electrical stimulation pulses may influence the reception of communication signals and/or the effectiveness of electrical stimulation pulses. Although it was described that each of communication module 102 and pulse generator module 104 may include switching circuitry, in some embodiments, LCP 100 may have a single switching module connected to the communication module 102, the pulse generator module 104, and electrodes 114 and/or 114'. In such embodiments, processing module 110 may control the switching module to connect modules 102/104 and electrodes 114/114' as appropriate.

In some embodiments, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby potentially increasing the battery life of LCP 100. In other instances, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip. In still other embodiments, processing module 110 may not be a single component. For example, processing module 110 may include multiple components positioned at disparate locations within LCP 100 in order to perform the various described functions. For example, certain functions may be performed in one component of processing module 110, while other functions are performed in a separate component of processing module 110.

Processing module 110, in additional embodiments, may include a memory circuit and processing module 110 may store information on and read information from the memory circuit. In other embodiments, LCP 100 may include a separate memory circuit (not shown) that is in communication with processing module 110, such that processing module 110 may read and write information to and from the separate memory circuit. The memory circuit, whether part of processing module 110 or separate from processing module 110, may be volatile memory, non-volatile memory, or a combination of volatile memory and non-volatile memory.

Energy storage module 112 may provide a power source to LCP 100 for its operations. In some embodiments, energy storage module 112 may be a non-rechargeable lithium-based battery. In other embodiments, the non-rechargeable battery may be made from other suitable materials. In some embodiments, energy storage module 112 may include a rechargeable battery. In still other embodiments, energy storage module 112 may include other types of energy storage devices such as capacitors or super capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. The one or more anchors 116 are shown schematically in FIG. 1. The one or more anchors 116 may include any number of fixation or anchoring mechanisms. For example, one or more anchors 116 may include one or more pins, staples, threads, screws, helix, tines, and/or the like. In some embodiments, although not shown, one or more anchors 116 may include threads on its external surface that may run along at least a partial length of an anchor member. The threads may provide friction between the cardiac tissue and the anchor to help fix the anchor member within the cardiac tissue. In some cases, the one or more anchors 116 may include an anchor member that has a cork-screw shape that can be screwed into the cardiac tissue. In other embodiments, anchor 116 may include other structures such as barbs, spikes, or the like to facilitate engagement with the surrounding cardiac tissue.

In some examples, LCP 100 may be configured to be implanted on a patient's heart or within a chamber of the patient's heart. For instance, LCP 100 may be implanted within any of a left atrium, right atrium, left ventricle, or right ventricle of a patient's heart. By being implanted within a specific chamber, LCP 100 may be able to sense cardiac electrical signals originating or emanating from the specific chamber that other devices may not be able to sense with such resolution. Where LCP 100 is configured to be implanted on a patient's heart, LCP 100 may be configured to be implanted on or adjacent to one of the chambers of the heart, or on or adjacent to a path along which intrinsically generated cardiac electrical signals generally follow. In these examples, LCP 100 may also have an enhanced ability to sense localized intrinsic cardiac electrical signals and deliver localized electrical stimulation therapy. In embodiments where LCP 100 includes an accelerometer, LCP 100 may additionally be able to sense the motion of the cardiac wall to which LCP 100 is attached.

Figure 2:
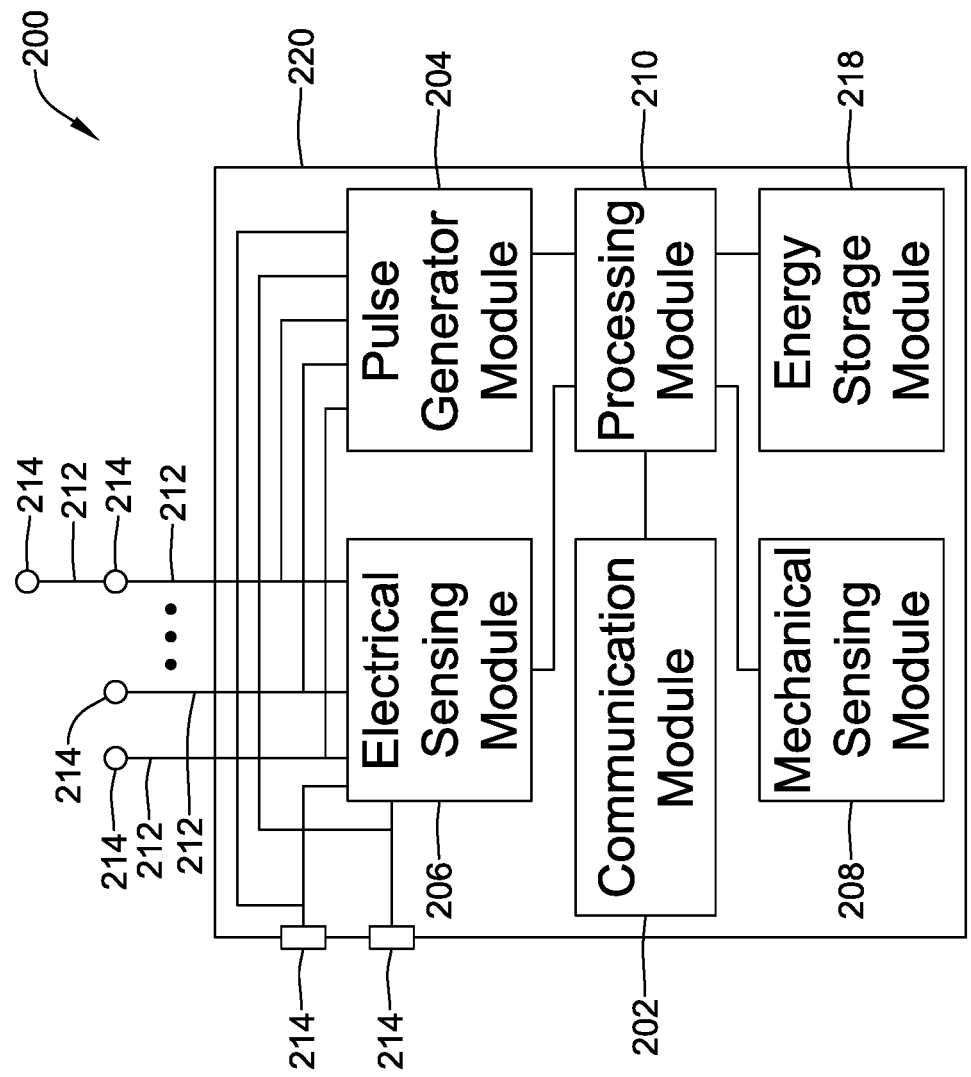
FIG. 2 is a schematic block diagram of another illustrative medical device that may be used in conjunction with the LCP of FIG. 1.

FIG. 2 depicts an embodiment of another device, medical device (MD) 200, which may operate to sense physiological signals and parameters and deliver one or more types of electrical stimulation therapy to tissues of the patient. In the embodiment shown, MD 200 may include a communication module 202, a pulse generator module 204, an electrical sensing module 206, a mechanical sensing module 208, a processing module 210, and an energy storage module 218. Each of modules 202, 204, 206, 208, and 210 may be similar to modules 102, 104, 106, 108, and 110 of LCP 100. Additionally, energy storage module 218 may be similar to energy storage module 112 of LCP 100. However, in some embodiments, MD 200 may have a larger volume within housing 220. In such embodiments, MD 200 may include a larger energy storage module 218 and/or a larger processing module 210 capable of handling more complex operations than processing module 110 of LCP 100.

While MD 200 may be another leadless device such as shown in FIG. 1, in some instances MD 200 may include leads, such as leads 212. Leads 212 may include electrical wires that conduct electrical signals between electrodes 214 and one or more modules located within housing 220. In some cases, leads 212 may be connected to and extend away from housing 220 of MD 200. In some embodiments, leads 212 are implanted on, within, or adjacent to a heart of a patient. Leads 212 may contain one or more electrodes 214 positioned at various locations on leads 212 and various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In other cases, the one or more of the electrodes 214 may be positioned subcutaneously but adjacent the patient's heart. The electrodes 214 may conduct intrinsically generated electrical cardiac signals to leads 212. Leads 212 may, in turn, conduct the received electrical cardiac signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical stimulation signals to the cardiac tissue of the patient (either directly or indirectly). MD 200 may also include one or more electrodes 214 not disposed on a lead 212. For example, one or more electrodes 214 may be connected directly to housing 220.

Leads 212, in some embodiments, may additionally contain one or more sensors, such as accelerometers, blood pressure sensors, heart sound sensors, blood-oxygen sensors, and/or other sensors which are configured to measure one or more physiological parameters of the heart and/or patient. In such embodiments, mechanical sensing module 208 may be in electrical communication with leads 212 and may receive signals generated from such sensors.

While not required, in some embodiments MD 200 may be an implantable medical device. In such embodiments, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body. In such embodiments, leads 212 may be implanted at one or more various locations within the patient, such as within the heart of the patient, adjacent to the heart of the patient, adjacent to the spine of the patient, or any other desired location.

In some embodiments, MD 200 may be an implantable cardiac pacemaker (ICP). In these embodiments, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some embodiments, MD 200 may additionally be configured to provide defibrillation/cardioversion therapy.

In some instances, MD 200 may be an implantable cardioverter-defibrillator (ICD). In such embodiments, MD 200 may include one or more leads implanted within a patient's heart. MD 200 may also be configured to sense electrical cardiac signals, determine occurrences of tachyarrhythmias based on the sensed electrical cardiac signals, and deliver defibrillation and/or cardioversion therapy in response to determining an occurrence of a tachyarrhythmia (for example by delivering defibrillation and/or cardioversion pulses to the heart of the patient). In other embodiments, MD 200 may be a subcutaneous implantable cardioverter-defibrillator (SICD). In embodiments where MD 200 is an SICD, one of leads 212 may be a subcutaneously implanted lead. In at least some embodiments where MD 200 is an SICD, MD 200 may include only a single lead which is implanted subcutaneously but outside of the chest cavity, however this is not required.

In some embodiments, MD 200 may not be an implantable medical device. Rather, MD 200 may be a device external to the patient's body, and electrodes 214 may be skin-electrodes that are placed on a patient's body. In such embodiments, MD 200 may be able to sense surface electrical signals (e.g. electrical cardiac signals that are generated by the heart or electrical signals generated by a device implanted within a patient's body and conducted through the body to the skin). MD 200 may further be configured to deliver various types of electrical stimulation therapy, including, for example, defibrillation therapy via skin-electrodes 214.

Figure 3:
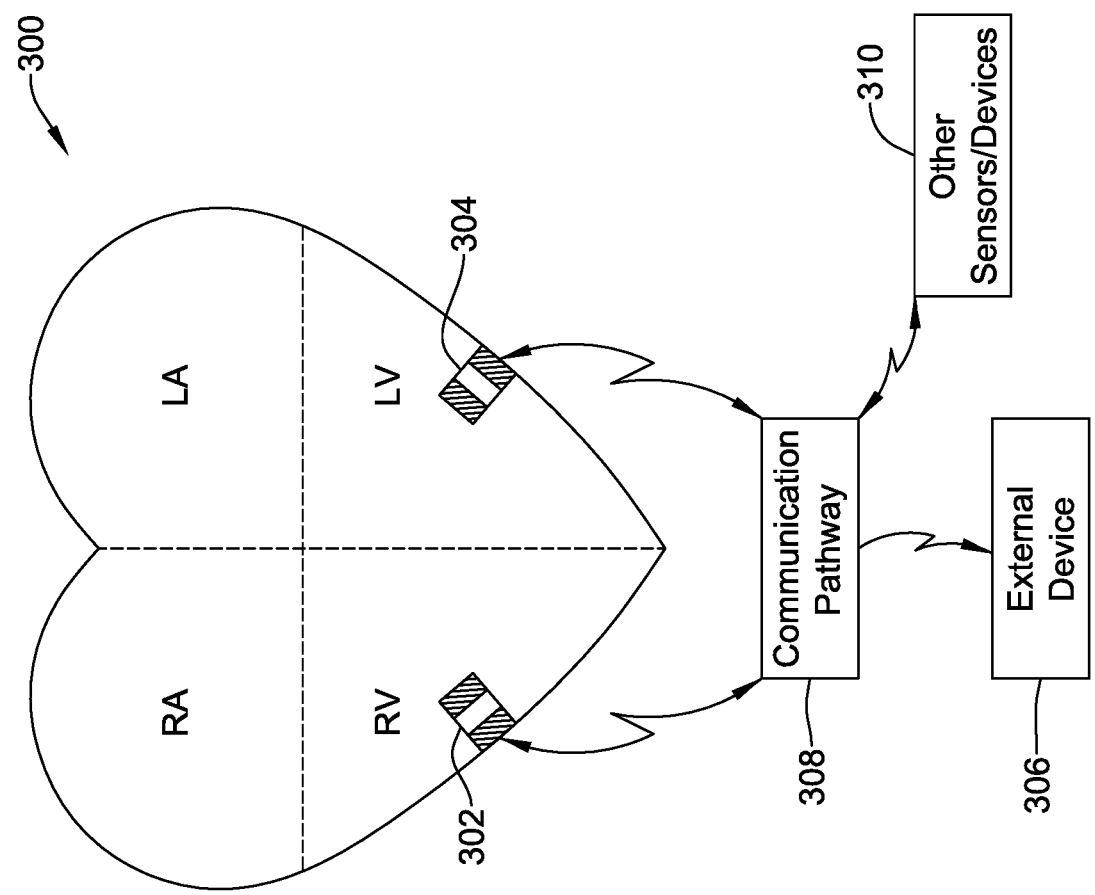
FIG. 3 is a schematic diagram of an illustrative medical system that includes multiple LCPs and/or other devices in communication with one another.

FIG. 3 illustrates an embodiment of a medical device system and a communication pathway through which multiple medical devices 302, 304, 306, and/or 310 of the medical device system may communicate. In the embodiment shown, medical device system 300 may include LCPs 302 and 304, external medical device 306, and other sensors/devices 310. External device 306 may be a device disposed external to a patient's body, as described previously with respect to MD 200. In at least some examples, external device 306 may represent an external support device such as a device programmer, as will be described in more detail below. Other sensors/devices 310 may be any of the devices described previously with respect to MD 200, such as ICPs, ICDs, and SICDs. Other sensors/devices 310 may also include various diagnostic sensors that gather information about the patient, such as accelerometers, blood pressure sensors, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one embodiment, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. One or more of devices 302/304, 306, and 310 of system 300 may additionally communicate command or response messages via communication pathway 308. The command messages may cause a receiving device to take a particular action whereas response messages may include requested information or a confirmation that a receiving device did, in fact, receive a communicated message or data.

It is contemplated that the various devices of system 300 may communicate via pathway 308 using RF signals, inductive coupling, optical signals, acoustic signals, or any other signals suitable for communication. Additionally, in at least some embodiments, the various devices of system 300 may communicate via pathway 308 using multiple signal types. For instance, other sensors/device 310 may communicate with external device 306 using a first signal type (e.g. RF communication) but communicate with LCPs 302/304 using a second signal type (e.g. conducted communication). Further, in some embodiments, communication between devices may be limited. For instance, as described above, in some embodiments, LCPs 302/304 may communicate with external device 306 only through other sensors/devices 310, where LCPs 302/304 send signals to other sensors/devices 310, and other sensors/devices 310 relay the received signals to external device 306.

In some cases, the various devices of system 300 may communicate via pathway 308 using conducted communication signals. Accordingly, devices of system 300 may have components that allow for such conducted communication. For instance, the devices of system 300 may be configured to transmit conducted communication signals (e.g. a voltage and/or current waveform punctuated with current and/or voltage pulses, referred herein as electrical communication pulses) into the patient's body via one or more electrodes of a transmitting device, and may receive the conducted communication signals via one or more electrodes of a receiving device. The patient's body may "conduct" the conducted communication signals from the one or more electrodes of the transmitting device to the electrodes of the receiving device in the system 300. In such embodiments, the delivered conducted communication signals may differ from pacing pulses, defibrillation and/or cardioversion pulses, or other electrical stimulation therapy signals. For example, the devices of system 300 may deliver electrical communication pulses at an amplitude/pulse width that is sub-threshold. That is, the communication pulses have an amplitude/pulse width designed to not capture the heart. In some cases, the amplitude/pulse width of the delivered electrical communication pulses may be above the capture threshold of the heart, but may be delivered during a refractory period of the heart and/or may be incorporated in or modulated onto a pacing pulse, if desired.

Additionally, unlike normal electrical stimulation therapy pulses, the electrical communication pulses may be delivered in specific sequences which convey information to receiving devices. For instance, delivered electrical communication pulses may be modulated in any suitable manner to encode communicated information. In some cases, the communication pulses may be pulse width modulated and/or amplitude modulated. Alternatively, or in addition, the time between pulses may be modulated to encode desired information. In some cases, a predefined sequence of communication pulses may represent a corresponding symbol (e.g. a logic "1" symbol, a logic "0" symbol, an ATP therapy trigger symbol, etc.). In some cases, conducted communication pulses may be voltage pulses, current pulses, bi-phasic voltage pulses, bi-phasic current pulses, tri-phasic voltage pulses, tri-phasic current pulses, quad-phasic voltage pulses, quad-phasic current pulses, hex-phasic voltage pulses, hex-phasic current pulses, or any other suitable electrical pulse as desired, as further detailed herein.

Figure 4:
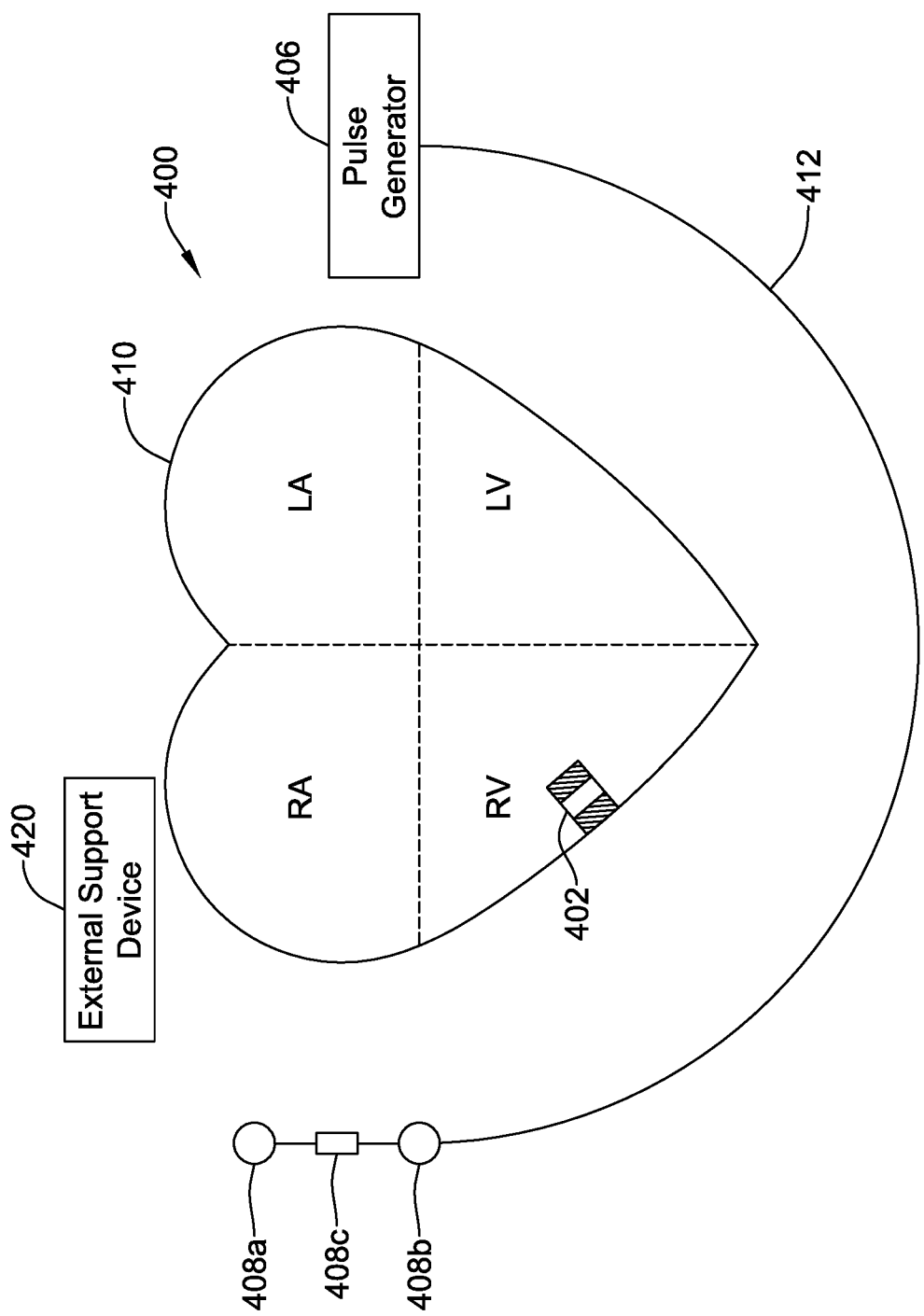
FIG. 4 is a schematic diagram of a system including an LCP and another medical device, in accordance with another embodiment of the present disclosure.

FIG. 4 depicts an illustrative medical device system 400 that may be configured to operate together. For example, system 400 may include multiple devices that are implanted within a patient and are configured to sense physiological signals, determine occurrences of cardiac arrhythmias, and deliver electrical stimulation to treat detected cardiac arrhythmias. In some embodiments, the devices of system 400 may be configured to determine occurrences of dislodgment of one or more devices of system 400. In FIG. 4, an LCP 402 is shown fixed to the interior of the right ventricle of the heart 410, and a pulse generator 406 is shown coupled to a lead 412 having one or more electrodes 408a-408c. In some cases, pulse generator 406 may be part of a subcutaneous implantable cardioverter-defibrillator (SICD), and the one or more electrodes 408a-408c may be positioned subcutaneously adjacent the heart. LCP 402 may communicate with the SICD, such as via communication pathway 308. The locations of LCP 402, pulse generator 406, lead 412, and electrodes 408a-c depicted in FIG. 4 are just illustrative.

In other embodiments of system 400, LCP 402 may be positioned in the left ventricle, right atrium, or left atrium of the heart, as desired. In still other embodiments, LCP 402 may be implanted externally adjacent to heart 410 or even remote from heart 410.

Medical device system 400 may also include external support device 420. External support device 420 can be used to perform functions such as device identification, device programming and/or transfer of real-time and/or stored data between devices using one or more of the communication techniques described herein, or other functions involving communication with one or more devices of system 400. As one example, communication between external support device 420 and pulse generator 406 can be performed via a wireless mode, and communication between pulse generator 406 and LCP 402 can be performed via a conducted communication mode. In some embodiments, communication between LCP 402 and external support device 420 is accomplished by sending communication information through pulse generator 406. However, in other embodiments, communication between the LCP 402 and external support device 420 may be via a communication module.

FIG. 4 only illustrates one example embodiment of a medical device system that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs with or without other devices such as pulse generator 406, with at least one LCP capable of delivering defibrillation therapy. Still another example may include one or more LCPs implanted along with a transvenous pacemaker and with or without an implanted SICD. In yet other embodiments, the configuration or placement of the medical devices, leads, and/or electrodes may be different from those depicted in FIG. 4. Accordingly, it should be recognized that numerous other medical device systems, different from system 400 depicted in FIG. 4, may be operated in accordance with techniques disclosed herein. As such, the embodiment shown in FIG. 4 should not be viewed as limiting in any way.

Figure 5B:
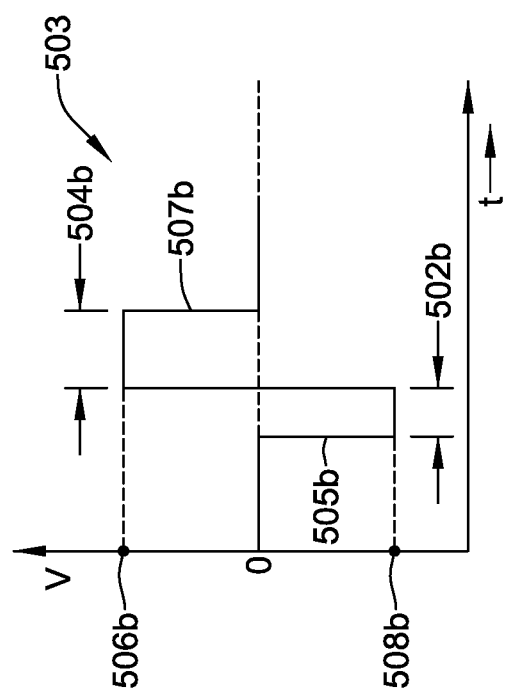
FIGS. 5A-5B depict illustrative biphasic conducted communication pulses with rectangular phase morphologies.
Figure 5A:
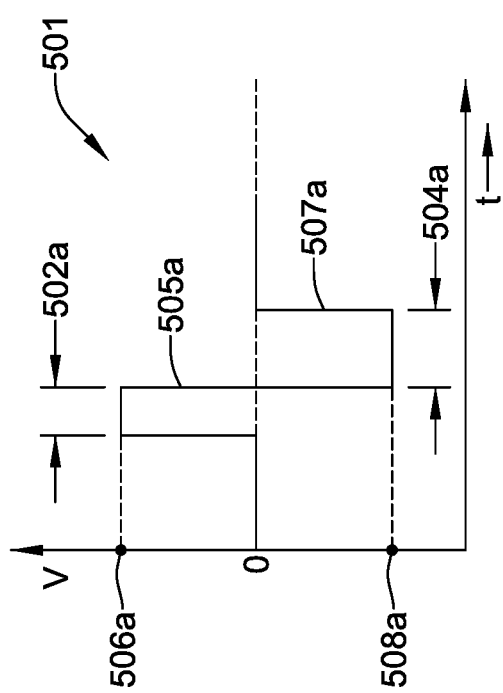
Figure 6A:
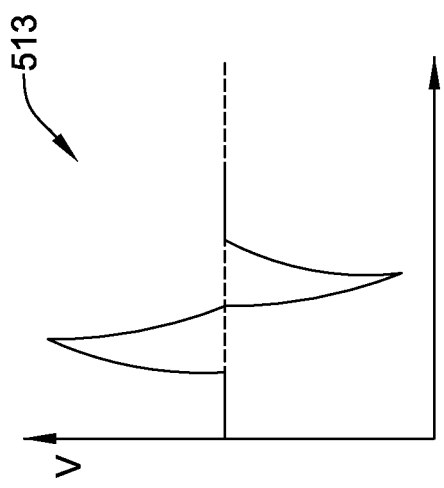
FIG. 6A depicts an illustrative biphasic conducted communication pulse width a saw-tooth phase morphology.
Figure 6B:
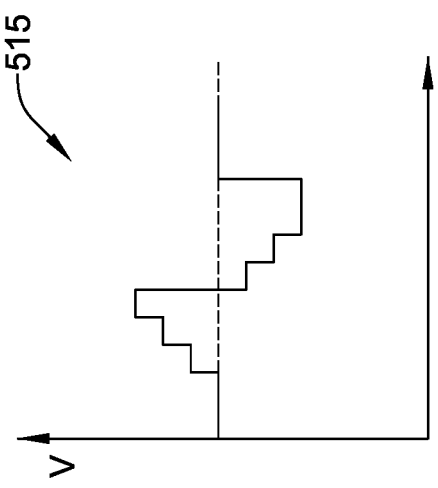
FIG. 6B depicts an illustrative biphasic conducted communication pulse width an exponential phase morphology.
Figure 6C:
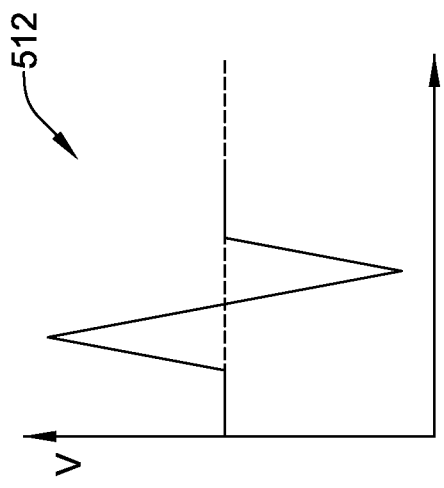
FIG. 6C depicts an illustrative biphasic conducted communication pulse width a trapezoid phase morphology.
Figure 6D:
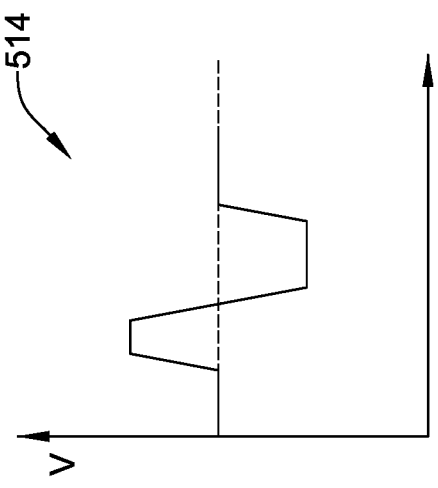
FIG. 6D depicts an illustrative biphasic conducted communication pulse width a stepped phase morphology.
Figure 7:
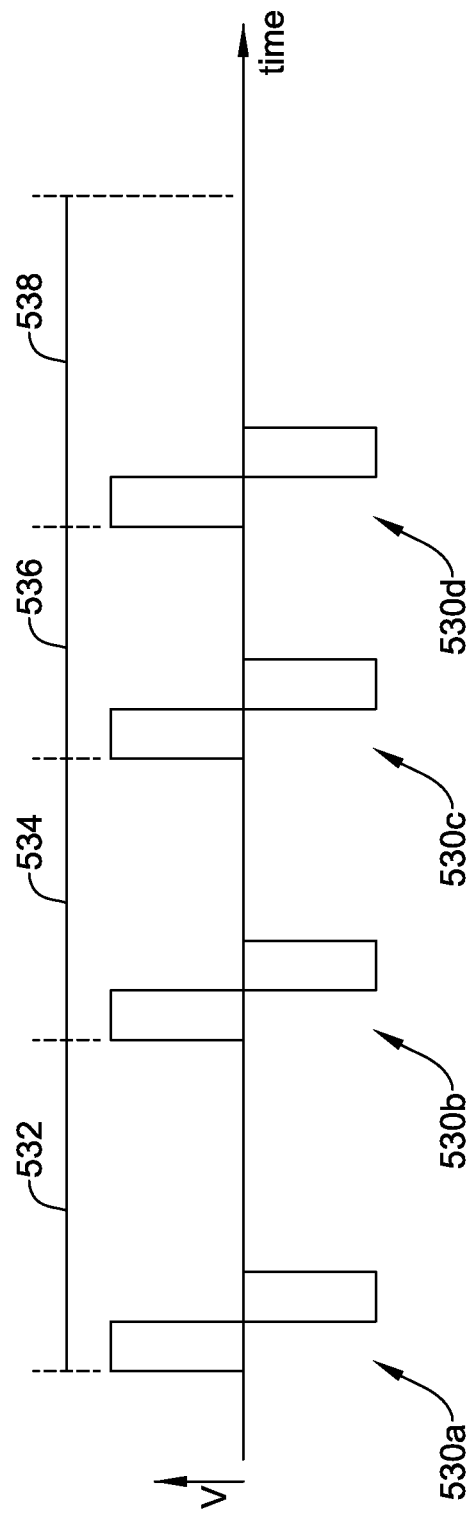
FIG. 7 depicts a communication pulse sequence demonstrating one illustrative information encoding scheme.
Figure 8:
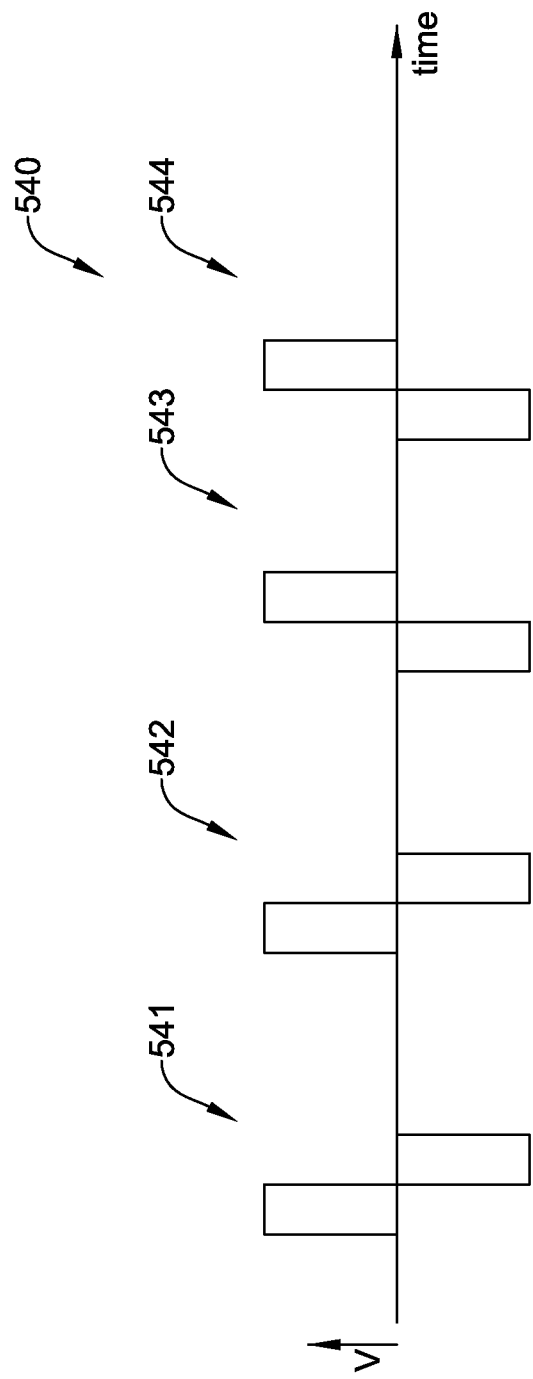
FIG. 8 depicts another communication pulse sequence demonstrating another illustrative information encoding scheme.

FIGS. 5A-B, 6A-6D, 9A-B, 10A-10B and 11A-11B depict example phasic communication pulses that may be used according to techniques of the present disclosure. Generally, these phasic conducted communication pulses intentionally differ from pacing pulses or other electrical stimulation therapy signals. The described phasic conducted communication pulses may have an amplitude/pulse width combination that is intentionally sub-threshold so as to not capture body tissue such as the heart. FIGS. 7-8 describe illustrative communication schemes suitable for convey information between devices using the illustrative phasic conducted communication pulses shown in FIGS. 5A-B, 6A-6D, 9A-B, 10A-10B and 11A-11B.

Generally, the phasic conducted communication pulses described herein may be either voltage pulses or current pulses. In a voltage pulse, the voltage amplitude is controlled and the current is dependent on the voltage amplitude and the resistance of the transmission medium. In a current pulse, the current amplitude is controlled and the voltage is dependent on the current amplitude and the resistance of the transmission medium. In some examples, the phasic conducted communication pulses may be combinations of voltage pulses and current pulses (e.g. some of the phases include a voltage pulse while other phases include a current pulse). It is contemplated that any of the devices described with respect to FIGS. 1-4 may include circuitry that generates such phasic conducted communication pulses.

FIGS. 5A-B depict first examples of phasic conducted communication pulses, including phasic conducted communication pulses 501, 503. As shown in FIGS. 5A-B, phasic conducted communication pulses 501, 503 may each include first phases 505*a*, 505*b* and second phases 507*a*, 507*b*. In these embodiments, each of first phases 505*a*, 505*b* may have a first polarity and each of second phases 507*a*, 507*b* may have a second polarity, with the first polarity and the second polarity being opposite. Example phasic conducted communication pulse 501 is depicted with first phase 505*a* having a positive polarity while second phase 507*a* has a negative polarity, while phasic conducted communication pulse 503 is depicted in an opposite manner.

First phases 505*a*, 505*b* may have amplitudes 506*a*, 506*b* and abbreviated pulse widths 502*a*, 502*b*. Second phases 507*a*, 507*b* may have amplitudes 508*a*, 508*b* and un-abbreviated pulse widths 504*a*, 504*b*. In these embodiments, pulse widths 502*a*, 502*b* of the first phases 505*a*, 505*b* may be considered 'abbreviate pulse widths' because their length are shown to be less than the length of pulse widths 504*a*, 504*b* of the second phases 507*a*, 507*b*. For example, abbreviated pulse widths 502*a*, 502*b* of the first phases 505*a*, 505*b* may have values that range between about five percent and about eighty percent of the value of un-abbreviated pulse widths 504*a*, 504*b* of the second phases 507*a*, 507*b*. The term "about" means ±10% of the specified value.

In some embodiments, pulse widths 504*a*, 504*b* of the second phases 507*a*, 507*b* may have values that range between about one microseconds and about seventy-five microseconds. In more specific embodiments, pulse widths 504*a*, 504*b* may have values that range between about one microseconds and about thirty microseconds, or may be about five microseconds, about ten microseconds, about fifteen microseconds, about twenty microseconds, about twenty-five microseconds, about thirty microseconds, about thirty-five microseconds, about forty microseconds, or any other suitable value. For a voltage pulse, the pulse width is the interval of time between the two times the voltage crosses 50% of the amplitude of the voltage pulse. For a current pulse, the pulse width is the interval of time between the two times the current crosses 50% of the amplitude of the current pulse.

Abbreviated pulse widths 502*a*, 502*b* may have values that range between about five percent and about eighty percent of the value of pulse widths 504*a*, 504*b*. In more specific embodiments, abbreviated pulse widths 502*a*, 502*b* may have values that range between about ten percent and about fifty percent of the value of pulse widths 504*a*, 504*b*, or be about ten percent, about twenty percent, about twenty-five percent, about thirty percent, about forty percent, about fifty percent, or any other suitable percentage of the value of pulse widths 504*a*, 504*b*.

In some cases, pulse widths 504*a* and 504*b* (or abbreviated pulse widths 502*a* and 502*b*), themselves, may not have exactly the same values. For instance, the values of pulse widths 504*a*, 504*b* (or abbreviated pulse widths 502*a*, 502*b*) may vary between successively delivered phasic conducted communication pulses. In some cases the values that differ between successively delivered phasic conducted communication pulses may vary by less than about ten percent.

In some instances, amplitudes 506*a*, 506*b*, 508*a*, and 508*b* may all be equal or about equal with amplitudes 508*a*, 508*b* having polarities (e.g. positive magnitude or negative magnitude relative to neutral or ground) opposite of amplitudes 506*a*, 506*b*. In general, amplitudes 506*a*, 506*b*, 508*a*, and 508*b* may be any suitable value, but in some specific embodiments, amplitudes 506*a*, 506*b*, 508*a*, and 508*b* may have values that range between about one volt and about fifteen volts. In further embodiments, amplitudes 506*a*, 506*b*, 508*a*, and 508*b* may have values that range between about two volts and about seven volts, or between about one volt and about four volts, or be equal to about one volt, about two volts, about three volts, about four volts, about five volts, about six volts, about seven volts, or any other suitable value. The specific amplitude values described with respect to the phasic conducted communication pulses may represent either peak amplitudes or Root Mean Square (RMS) amplitudes.

In some cases, the amplitudes 506a, 506b may not be equal to amplitudes 508a, 508b, respectively, but for differences in polarity. For instance, in at least some embodiments, amplitudes 506a, 506b may have values that are between about seventy-five percent and about ninety-nine percent of the values of amplitudes 508a, 508b, respectively. In still further embodiments, amplitudes 508a, 508b may have the smaller values. In still further additional or alternative embodiments, amplitudes 506a, 506b, 508a, and/or 508b may vary between successively delivered phasic conducted communication pulses. For instance, the values of amplitudes 506a, 506b, 508a, and 508b may vary by less than about ten percent between successively delivered phasic conducted communication pulses.

Alternatively, or in addition to that described above, it is contemplated that the amplitudes 505a, 505b of the abbreviated phases 505a, 505b may differ from the amplitudes 508a, 508b of unabbreviated phases 507a, 507b in order to help control charge accumulation on excitable tissue and reduce the likelihood that the unabbreviated phases 507a, 507b will stimulate the tissue. In one specific example, with reference to FIG. 5A, pulse width 502a may be equal or about equal to pulse width 504a, and the absolute value of the amplitude 506a may be less than (e.g. abbreviated) the absolute value of the amplitude 508a. In some cases, both the pulse width and amplitude of the abbreviated phases 505a, 505b and unabbreviated phases 507a, 507b may be set to help control charge accumulation on excitable tissue and thus reduce the likelihood that the unabbreviated phases 507a, 507b will stimulate the tissue.

Although FIGS. 5A-B depict bi-phasic conducted communication pulses 501, 503 with first phases 505a, 505b and second phases 507a, 507b having generally rectangular morphologies, it should be understood that the techniques of the present disclosure are not limited to these particular morphologies of first phases 505a, 505b and second phases 507a, 507b. FIGS. 6A-6D depict other illustrative pulses with different phase morphologies. FIG. 6A depicts a bi-phasic conducted communication pulse 512 with saw-tooth phases. FIG. 6B depicts a bi-phasic conducted communication pulse 513 with exponential phases. FIG. 6C depicts a bi-phasic conducted communication pulse 514 with trapezoid phases. FIG. 6D depicts a bi-phasic conducted communication pulse 515 with stepped phases. It is contemplated that bi-phasic conducted communication pulses that are substantially similar to these may be used. In this regard, a first pulse phase is considered substantially similar to a second pulse phase if the area between the first pulse phase and the second pulse phase is less than 10% of the area under the second pulse phase, with the amplitude and duration of the first pulse phase normalized to the second pulse phase. It should be understood that these are only example pulse shapes. It is contemplated that any suitable pulse shape may be used. In general, an abbreviated leading pulse may indispose the tissue to excitation (e.g. capture) by the successive pulse(s). In some cases, a trailing abbreviated pulse (e.g. see FIGS. 9A-9B, 10A-10B, 11A-11B) may be used for charge balance, or further excitation inhibition. It is contemplated that such pulses may have any suitable form of voltage or current vs time, as long as a leading pulse contributes charge to the tissue in a manner that inhibits excitation (e.g. hyperpolarization).

Although FIGS. 6A-D depict phasic conducted communication pulses having differing phase morphologies than the phase morphologies of FIGS. 5A-B, the two separate phases of each phasic conducted communication pulse of FIGS. 6A-D may have similar values to those described with respect to first phases 505a, 505b and second phases 507a, 507b. Notably, in FIGS. 6A-D, a first phase is shown preceding a second phase, with the duration of the first phase being abbreviated with respect to the second phase. Also, although each phasic conducted communication pulse 512-515 of FIGS. 6A-D is only shown with a single polarity orientation, it should be understood that phasic conducted communication pulses 512-515 may be implemented with the opposite polarity orientation, if desired. Moreover, it is contemplated that, in short pulse durations (e.g. less than 60 microseconds or less), a longer pulse may be provided first, followed by a shorter pulse to neutralize the charge on the tissue before activation of the tissue occurs.

FIGS. 7 and 8 depict different example communication schemes that may be used by devices of a system, such as system 400, with the phasic conducted communication pulses described with respect to FIGS. 5A-6D and elsewhere in this disclosure. For ease of description, only rectangular phasic conducted communication pulses are shown, but it should be understood that the disclosed techniques are independent of phasic conducted communication pulses morphology.

FIG. 7 shows a graph of four example phasic conducted communication pulses 530a-d. Phasic conducted communication pulses 530a-d are separated by three distinct time periods, 532, 534, and 536, respectively. In the example shown, the last time period 538 does not separate one communication pulse 530d from another communication voltage pulse. Rather, time period 538 is simply a threshold length of time extending from communication pulse 530d, without a subsequent communication voltage 530 occurring before the end of the threshold length of time. This can signal an end-of-frame (EOF).

In some cases, devices of a system using the phasic conducted communication pulses and the techniques described herein may identify communication symbols based on the length of time between phasic conducted communication pulses 530a-d. For example, if the time between two consecutive phasic conducted communication pulses falls within a first time range, then a first symbol may be identified by the receiver. If the time between two phasic conducted communication pulses falls within a second time range, then a second symbol may be identified by the receiver. If the time between two phasic conducted communication pulses falls within a third time range, then a third symbol may be identified by the receiver, and so on. In one example, a sync symbol is identified when the time between two phasic conducted communication pulses falls within a range of 800-1100 microseconds, a "1" symbol is identified when the time between two phasic conducted communication pulses falls within a range of 550-700 microseconds, and a "0" symbol is identified when the time between two phasic conducted communication pulses falls within a range of 350-450 microseconds. In some cases, the "0" and "1" symbols correspond to "0" and "1" bits, respectively, as the devices of the system may operate in a base two number system. These are just examples. It is contemplated that any number of different symbols may be included in the communication protocol, with different symbols assigned to different times or time ranges. In some case, if a phasic conducted communication pulse is not followed by another phasic conducted communication pulse within a threshold amount of time (e.g. time period 538), an end or frame (EOF) symbol may be identified. The threshold amount of time (e.g. time period 538) may be, for example, 1250 microseconds or more.

In some cases, the time between phasic conducted communication pulses may be tracked using an internal clock. It is contemplated that the sending device may include an internal clock that oscillates at a clock frequency. Likewise, the receiving device may include an internal clock that oscillates at the same (or different) clock frequency. When so provided, each symbol to be communicated may be assigned a different number of clock cycles between phasic conducted communication pulses. For example, a synchronization symbol may be assigned 24 clock cycles, which for a clock frequency of 25.6 kHz, would correspond to a delay between phasic conducted communication pulses of about 938 microseconds. A range may be provided to help compensate for noise, temperature changes, voltage variances, clock drift, etc. The range may be, for example, +/−10%, or in the example given above, may be from about 844 microseconds to about 1032 microseconds. A "1" symbol may be assigned to 16 clock cycles, which for a clock frequency of 25.6 kHz, would corresponds to a delay between phasic conducted communication pulses of about 625 microseconds. A range may be provided around this figure to help compensate for noise, temperature changes, voltage variances, clock drift, etc. The range may be, for example, +/−10%, or in the example given above, may be from about 563 microseconds to about 688 microseconds. Likewise, a "0" symbol may be assigned to 10 clock cycles, which for a clock frequency of 25.6 kHz, would correspond to a delay between phasic conducted communication pulses of about 391 microseconds. A range may be provided around this figure to help compensate for noise, temperature changes, voltage variances, clock drift, etc.

To transmit a desired symbol, the sending device may provide a first phasic conducted communication pulse, then count the number of clock cycles that corresponds to the desired symbol (e.g. 16 clock cycles for a "1" symbol), and then provide a phasic conducted communication pulse. When the receiving device receives the first phasic conducted communication pulse, the receiving device may start counting internal clock cycles. When the second phasic conducted communication pulse is received, the receiving device may stop counting clock cycles. The receiving device may then compare the number of counted internal clock cycles to the number of clock cycles assigned to each symbol. When a match is found, the desired symbol is identified by the receiving device.

In some cases, the accuracy of the internal clocks in the sending device and/or receiving device may degrade over time. Due to this degradation, the devices of the system may begin to determine lengths of time differently with respect to absolute lengths of time, and possibly with respect to each other if the clocks of the devices degrade differently with respect to each other. Accordingly, in examples where time periods 532, 534, 536, and 538 are ranges of times, the devices of the system may still correctly interpret symbols even after some level of clock degradation.

In some cases, the devices of the system may be configured to reconfigure their internal clocks on a periodic or other basis. For example, a first device may broadcast a beginning calibration signal, an ending calibration signal, and the length of time between the two signals as determined by the broadcasting device. Each other device may then calibrate their internal clocks so that the time period between the two calibration signals is equal to the length of time sent by the broadcasting device. Such a reconfiguration may help ensure that a clock of a device does not drift too far relative to that of other devices of the system such that the device becomes functionally inoperative.

Whatever the exact lengths of time periods 532, 534, 536, and 538, in some examples, time period 532 may be longer than either of time periods 534 and 536. In such examples, this arrangement may prevent accidental transmission of one or more symbols from one device to another device, or a device interpreting noise as communication of one or more symbols. For instance, the devices of the system may transmit phasic conducted communication pulses to communicate a synchronization symbol before transmitting one or more other symbols, and receiving devices may ignore any other symbols received before receiving a synchronization symbol. In some situations, a receiving device may receive a first, true phasic conducted communication pulse but then receive noise after a length of time shorter than time period 532. If the noise is similar in morphology to a phasic conducted communication pulse, the receiving device may interpret the noise as a phasic conducted communication pulse. However, since the noise occurred after a shorter length of time than time period 532, even if the noise occurred at a length of time indicating a "0" symbol or a "1" symbol, the receiving device would ignore those symbols as the receiving device had not yet received a synchronization symbol. In this manner, the devices of the system may suppress erroneously transmitted or falsely interpreted symbols.

In some instances, a blanking period may be applied by the receiving device immediately following receiving each phasic conducted communication pulse. During the blanking period, the receiving device may ignore any received communication signals. This may help further reduce noise that might arise immediately after a phasic conducted communication pulse from being interpreted as a valid phasic conducted communication pulse. The blanking period may be anywhere between one-quarter to three-quarters the length of time period 532, or any other suitable length of time. In one example, the blanking period may be, for example about 250 microseconds. In some cases, the sending device may apply a similar blanking period, during and/or following the transmission of a phasic conducted communication pulse. Such a blanking period may help prevent the circuitry of the sending device, which senses for phasic conducted communication pulses from other devices, from sensing the phasic conducted communication pulses generated by the sending device.

In FIG. 7, the receiving device(s) of the system may identify the elapse time 532 between communication pulses 530a and 530b, and interpret that elapse time 532 as, for example, a synchronization symbol. Likewise, the receiving device(s) of the system may identify the elapse time 534 between communication pulses 530b and 530c, and interpret that elapse time 534 as, for example, a "1" symbol. Moreover, the receiving device(s) of the system may identify the elapse time 536 between communication pulses 530c and 530d, and interpret that elapse time 536 as, for example, a "0" symbol. In some cases, the receiving device(s) of the system may detect that communication pulse 530d is not followed by another phasic conducted communication pulse within the threshold amount of time 538, and may interpret that as an End of Frame (EOF) symbol. This particular example is only illustrative, and it is contemplated that different symbols, different time delays and different sequences may be used, depending on the application.

In some examples, the devices of the system are continuously (although possibly punctuated by blanking periods) listening for phasic conducted communication pulses. That is, the devices of the system may not send out wake-up signals or establish specific communication connections before sending out phasic conducted communication pulses to other devices. Instead, the devices of the system may rely on synchronization pulses as a signal to the other devices of the system that the sending device is sending a message. In some cases, an EOF symbol may be a signal that the sending device has communicated the entire message.

In the example of FIG. 7, time periods 532, 534, 536, and 538 are depicted as being measured from a leading edge of each communication pulse 530. However, in other examples, time periods 532, 534, 536, and 538 may be measured off of other features of phasic conducted communication pulses 530. For instance, the devices of the system may measure time periods 532, 534, 536, and 538 from the trailing edge of phasic conducted communication pulses 530. In still other examples, the devices of the system may measure time periods 532, 534, 536, and 538 from the inflection point of phasic conducted communication pulses 530. Additionally, the devices of the system may not begin measuring a time period from a feature of phasic conducted communication pulses 530, for example the leading edge, until the amplitude of the phasic conducted communication pulse reaches a threshold level. In some cases, the devices of the system may measure time periods 532, 534, 536, and 538 from a zero-crossing point of phasic conducted communication pulses 530. These are just some examples.

In some of these embodiments, the devices of the system may ensure that the same total amount of positive magnitude energy (e.g. voltage or current) is delivered into the body of the patient during communication as negative magnitude energy. This may help ensure that the communication scheme is charge balanced. Although, in some embodiments, the communication scheme may not be charge balanced. A communication scheme may be considered substantially charge balanced where the total area under the curves of the positive magnitude phases of the phasic conducted communication pulses of a sent or received communication sequence are within ten percent, either above or below, the total area of the negative magnitude phases of the phasic conducted communication pulses of the sent or received communication sequence.

In order to effect a charge balanced, or substantially charge balanced, communication sequence, a sending device may invert the polarity of every other delivered phasic conducted communication pulse. For instance, in the example described above, phasic conducted communication pulse 530a may look like phasic conducted communication pulse 501, and communication pulse 530b may look like phasic conducted communication pulse 503, e.g. having opposite polarity compared to phasic conducted communication pulse 501. Accordingly, where phasic conducted communication pulses 530a, 530b have the same dimensions with respect to each of their respective phases, but flip the polarity of each of the phases, any string of an even number of phasic conducted communication pulses will be charge balanced, and any string of an odd number of phasic conducted communication pulses, while not perfectly charge balanced, will be substantially charge balanced. Alternatively, a last phasic conducted communication pulses may be appended to any string of an odd number of phasic conducted communication pulses to create an even numbered string.

FIG. 8 depicts another illustrative communication scheme that may be implemented with the phasic conducted communication pulses disclosed herein. Instead of varying the length of time between successive phasic conducted communication pulses, the scheme of FIG. 8 may use differences in the polarity of the phasic conducted communication pulses to encode information.

The example of FIG. 8 depicts a sequence of pulses 540. Sequence of pulses 540 includes phasic conducted communication pulses 541-544. Phasic conducted communication pulses 541 and 542 have a first polarity, with their first phases having a positive polarity and their second phases having a negative polarity, while phasic conducted communication pulses 543 and 544 have a second polarity with their first phases having a negative polarity and their second phases having a positive polarity. In the example of FIG. 8, one of the first or second polarities may be associated with a '0' symbol, and the other of the first or second polarities may be associated with a '1' symbol. In this manner, where the devices using the communication scheme of FIG. 8 operate according to binary number system, the devices may communicate information using sequences of phasic conducted communication pulses, which each phasic conducted communication pulse denoting either '0' or '1'. For instance, in the example of FIG. 8 where the first polarity is associated with '0' and the second polarity is associated with '1', sequence of pulses 540 may read '0011' according to this communication scheme.

As with the example of FIG. 7, it may be beneficial for a sent communication to be charge balanced or substantially charge balanced. However, in the example of FIG. 8, since the polarity of the phasic conducted communication pulses represents information, a sending device may not be able to use the charge balancing scheme described with respect to FIG. 7. Instead, a sending device may determine how many more phasic conducted communication pulses having one of the polarities the device sent than the other polarity. For instance, if the sending device sent a sequence of phasic conducted communication pulses including four phasic conducted communication pulses having the first polarity and two phasic conducted communication pulses having the second polarity, the device may determine that the device sent two more phasic conducted communication pulses having the first polarity than the second polarity. The sending device may then deliver a sequence of pulses including two phasic conducted communication pulses having the second polarity. The receiving device may know to ignore every other sequence of pulses delivered from a sending device as a charge balancing sequence. In some embodiments, the sending device may not send any charge balancing sequence of pulses if the difference between the number of pulses delivered having the first polarity and the second polarity (or having the second polarity and the first polarity) is below a threshold number of pulses. In these embodiments, the sending device may determine that the communicated sequence of pulses is substantially charge balanced such that no charge balancing sequence of pulses is necessary.

Figure 9B:
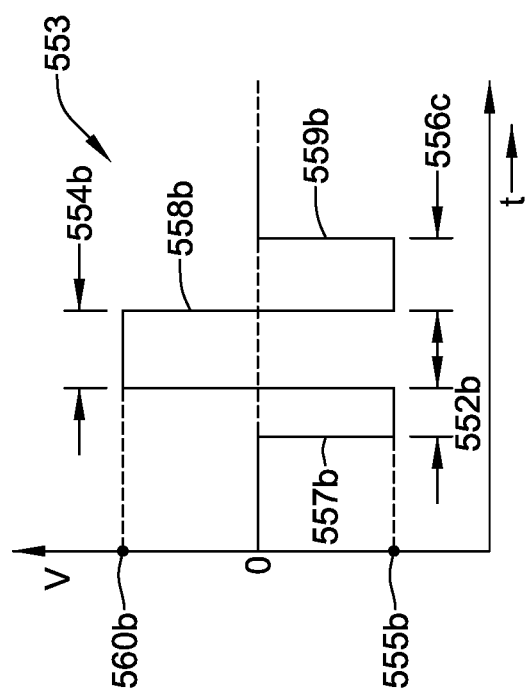
FIGS. 9A-9B depict illustrative tri-phasic conducted communication pulses.
Figure 9A:
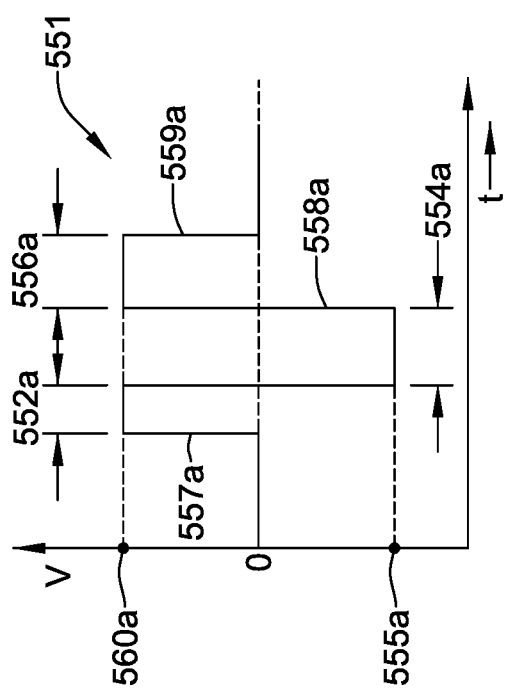

FIGS. 9A-B depict still further illustrative phasic conducted communication pulses, phasic conducted communication pulses 551, 553, that may be used in accordance with the present disclosure. Generally, phasic conducted communication pulses 551, 553 may be similar to phasic conducted communication pulses 501, 503 except that phasic conducted communication pulses 551, 553 include three phases instead of two.

As can be seen in FIGS. 9A-B, phasic conducted communication pulses 551, 553 include first phases 557a, 557b, second phases 558a, 558b, and third phases 559a, 559b. First phases 557a, 557b have abbreviated pulse widths 552a, 552b, while second phases 558a, 558b and third phases 559a, 559b having non-abbreviated pulse widths 554a, 554b and 556a, 556b. As in the embodiments of FIGS. 5A-B, abbreviated pulse widths 552a, 552b may have values that represent a portion of the values of non-abbreviated pulse widths 554a, 554b and 556a, 556b. In general, the values and proportions described with respect to abbreviated pulse widths 502a, 502b and pulse widths 504a, 504b of phasic conducted communication pulses 501, 503 may apply equally to abbreviated pulse widths 552a, 552b and non-abbreviated pulse widths 554a, 554b and 556a, 556b. However, in at least some embodiments, pulse widths 554a and 556a, and/or pulse widths 554b and 556b may not be equal. In some cases, this difference may between about one percent and about eighty percent, between about one percent and about fifty percent, about one percent and about thirty percent, about one percent and about ten percent. In some cases, pulse width 556a may be less than pulse width 554a by an amount that is about equal to abbreviated pulse width 552a, and pulse width 556b may be less than pulse width 554b by an amount that is about equal to abbreviated pulse width 552b.

Additionally, phases 557a and 559a of phasic conducted communication pulse 551 may have the same amplitude, amplitude 560a, while phase 558a has amplitude 555a. In some embodiments, amplitudes 560a and 555a may be equal but opposite in magnitude (e.g. opposite polarity about neutral or ground). However, in other embodiments, amplitudes 560a and 555a may differ, sometimes by less than ten percent. In some cases, amplitudes 560b and 555b may be equal but opposite in magnitude (e.g. opposite polarity about neutral or ground). However, in other embodiments, amplitudes 560b and 555b may differ, sometimes by less than ten percent. In some cases, phases 557a and 559a may have the same or different amplitudes, but both still having positive magnitude amplitudes (e.g. same polarity). In some cases, the amplitudes of phases 557a and 559a may differ by less than ten percent.

In each of the embodiments of FIGS. 5A-6B and FIGS. 9A-B, each of the disclosed phasic conducted communication pulses were not necessarily charge balanced. That is, each of the phasic conducted communication pulses may not include an area under those portions of the phasic conducted communication pulses that have a positive polarity do not necessarily equal those portions of the phasic conducted communication pulse that have a negative polarity. In some embodiments, it may be beneficial to employ inherently charge balanced phasic conducted communication pulses so that there is no need for charge balancing by counting differences between the delivered numbers of different polarity phasic conducted communication pulses or by flipping the polarity of each successively delivered phasic conducted communication pulse.

Figure 10B:
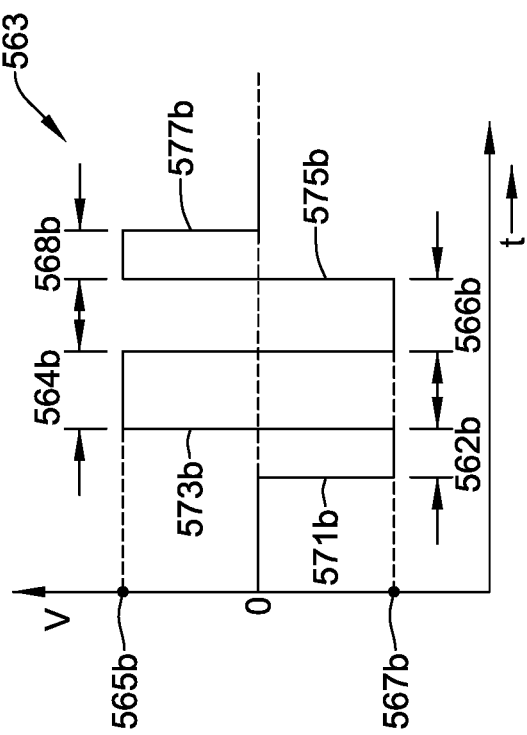
FIGS. 10A-10B depict illustrative quad-phasic conducted communication pulses.
Figure 10A:
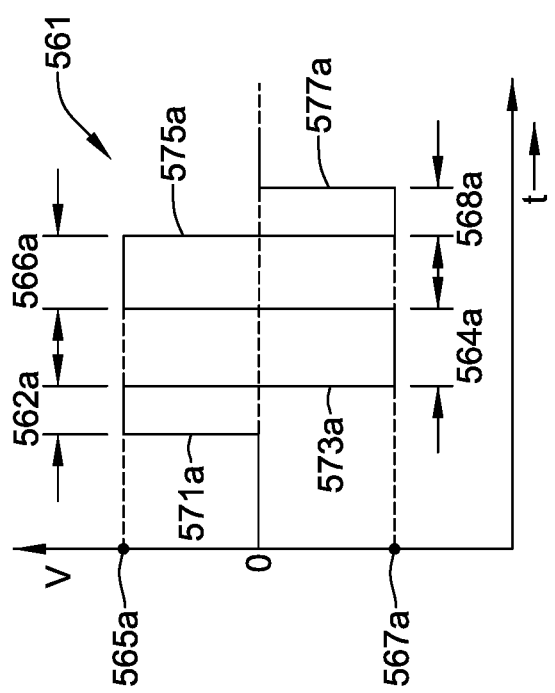

FIGS. 10A-B depict a quad-phasic phasic conducted communication pulse that is shown to be charge balanced. FIGS. 10A-B depict phasic conducted communication pulses 561, 563, respectively. Each of phasic conducted communication pulses 561, 563 has first phases 571a, 571b, second phases 573a, 573b, third phases 575a, 575b, and fourth phases 577a, 577b. Each of first phases 571a, 571b, second phases 573a, 573b, third phases 575a, 575b, and fourth phases 577a, 577b have a corresponding amplitude and pulse width. In the example shown, first phases 571a, 571b and fourth phases 577a, 577b have abbreviated pulse widths 562a, 562b and 568a, 568b, while second phases 573a, 573b and third phases 575a, 575b have non-abbreviated pulse widths 564a, 564b, and 566a, 566b. Generally, pulse widths 564a, 564b, and 566a, 566b may have values similar to those described with respect to other phasic conducted communication pulses described herein. Additionally, abbreviated pulse widths 562a, 562b and 568a, 568b may also have values, or proportions to pulse widths 564a, 564b, and 566a, 566b, similar to those values described herein with respect to other phasic conducted communication pulses. Additionally, amplitudes 565a, 565b, and 567a, 567b may have similar values to those amplitudes described with respect to previously described phasic conducted communication pulses.

Where abbreviated pulse widths 562a, 562b and 568a, 568b are equal to each other and pulse widths 564a, 564b, and 566a, 566b are equal to each other, phasic conducted communication pulses 561, 563 will be charge balanced as the areas under first phases 571 and fourth phases 577 will equal the areas under second phases 573 and third phases 575. However, in other embodiments, there may be variations between different phases of phasic conducted communication pulses 561, 563. In these embodiments, where there is a difference of less than ten percent between the areas under first phases 571 and fourth phases 577 and the areas under second phases 573 and fourth phases 577, phasic conducted communication pulses 561, 563 may still be considered substantially charge balanced. Over time, these small differences may not adversely impact the patient in which the devices using phasic conducted communication pulses 561, 563 are implanted.

Figure 11B:
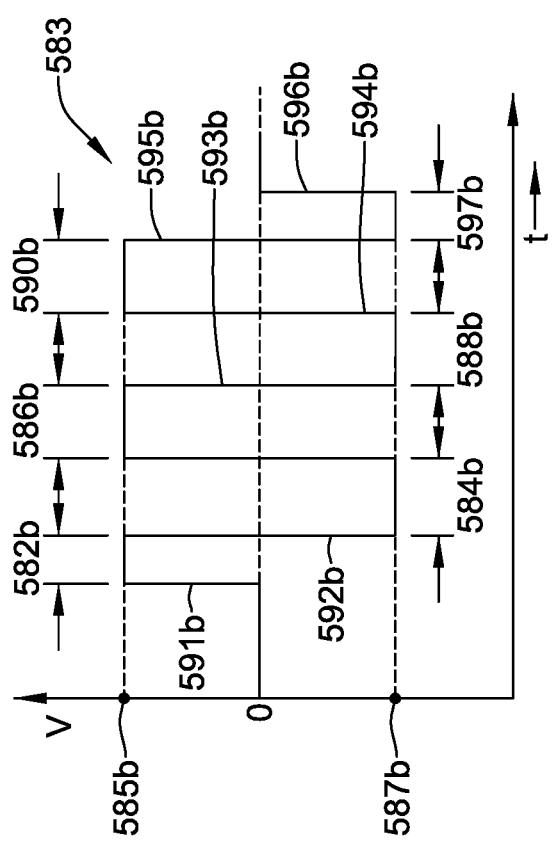
FIGS. 11A-11B depict illustrative hexa-phasic conducted communication pulses.
Figure 11A:
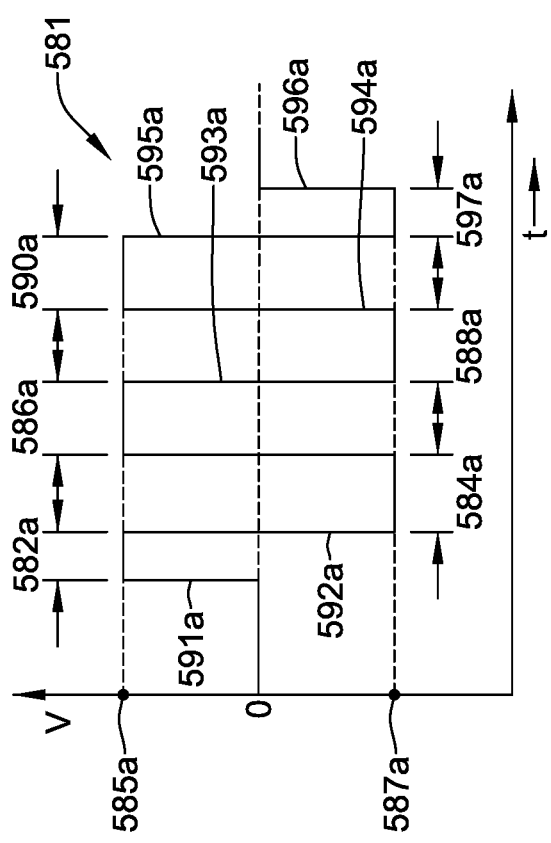

Additional illustrative charged balanced phasic conducted communication pulses are depicted in FIGS. 11A-B. Phasic conducted communication pulses 581, 583 are hexa-phasic conducted communication pulses. Phasic conducted communication pulse 581 includes first phase 591a, second phase 592a, third phase 593a, fourth phase 594a, fifth phase 595a and sixth phase 596a. Phasic conducted communication pulse 583 583 includes first phase 591b, second phase 592b, third phase 593b, fourth phase 594b, fifth phase 595b, and sixth phase 596b. Each of these phases 591a-596a and 591b-596b include pulse widths 582a, 582b, 584a, 584b, 586a, 586b, 588a, 588b, 590a, 590b, and 597a, 597b as shown. Further, each of phases 591a-596a and 591b-596b have amplitudes 585a, 585b or 587a, 587b, also as shown.

In at least some embodiments, pulse widths 582a, 582b, 584a, 584b, 590a, 590b, and 597a, 597b may be abbreviated pulse widths, to one degree or another. For instance, abbreviated pulse widths 584a, 584b and 590a, 590b may have similar values and/or proportions to those described with respect to abbreviated pulse widths 502a, 502b. Abbreviated pulse widths 582a, 582b and 597a, 597b may have different values or proportions. For instance, abbreviated pulse widths 584a, 584b and 590a, 590b may have values that range between about five percent and about eighty percent of the value of pulse widths 586a, 586b and/or 588a, 588b. In more specific embodiments, abbreviated pulse widths 582a, 582b and 597a, 597b may have values that range between about ten percent and about fifty percent of the value of pulse widths 586a, 586b and/or 597a, 597b or be about ten percent, about twenty percent, about twenty-five percent, about thirty percent, about forty percent, about fifty percent, or any other suitable percentage of the value of pulse widths

586a, 586b and/or 597a, 597b. Abbreviated pulse widths 582a, 582b and 597, on the other hand, may have values that range between about one percent and about twenty-five percent of the values of pulse widths 586a, 586b and/or 597a, 597b.

In a similar manner to phasic conducted communication pulses 561, 563, phasic conducted communication pulses 581, 583 may be charge balanced when the phases 591a-593a and 591b-593b having a first polarity are symmetrical with the corresponding phases 594a-596a and 594b-596b having a second opposite polarity. However, even in embodiments where the phases having the first polarity are not perfectly symmetrical with the phases having the second polarity, phasic conducted communication pulses 581, 583 may still be considered substantially charge balanced if the total area of the phases having the first polarity is within about ten percent of the total area of the phases having the second polarity.

Figure 12:
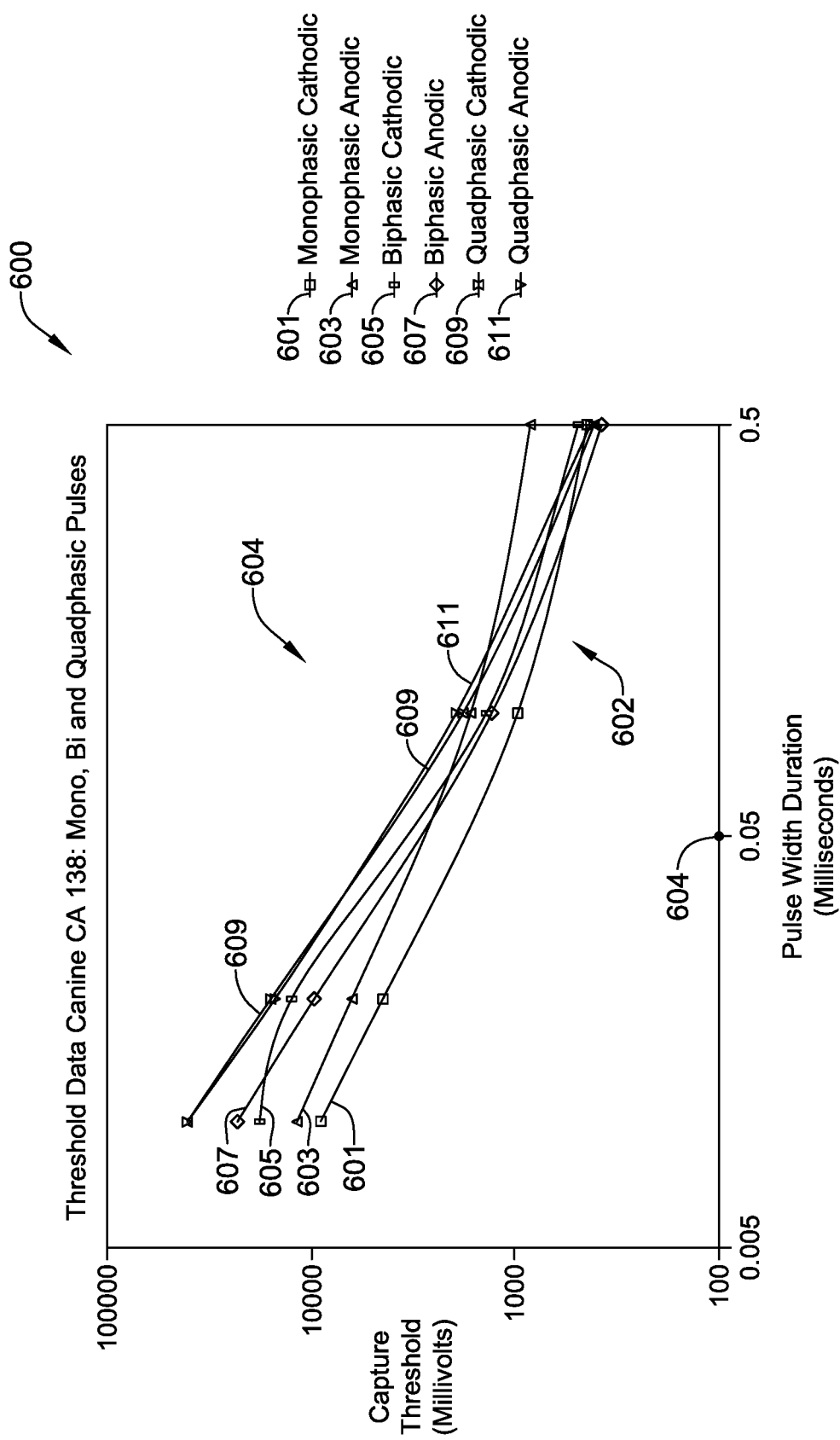
FIG. 12 shows a graph of data collected from a canine showing the heart capture threshold versus pulse width duration for various different pulse morphologies.

The specific values for the pulse widths of the different disclosed phasic conducted communication pulses may be chosen based on a study carried out on a canine. FIG. 12 shows a graph 600 of data collected from a canine study showing heart capture threshold versus pulse width duration for various different communication pulse morphologies including mono-phasic, bi-phasic, and quad-phasic). It is desirable to not capture the heart of the canine with the communication pulses. As such, a higher capture threshold is desirable.

Graph 600 depicts lines 601, 603, 605, 607, 609, and 611 on a log-log plot of pulse widths (x-axis) versus the amplitude at which the pulse caused stimulation (i.e. capture) of the heart tissue. Line 601 represents results for a mono-phasic pulse having a first polarity (cathodic polarity) while line 603 represents results for a mono-phasic pulse having a second polarity (anodic polarity), which is opposite the first polarity. Lines 605 and 607 depict results for bi-phasic pulses having opposite polarities, and lines 609 and 611 depict results for quad-phasic pulses having opposite polarities.

The pulse width duration values of the x-axis of graph 600 represent the values for the non-abbreviated pulse width. For instance, with respect to the quad-phasic pulses, the pulse width duration values correspond to the values of pulse widths 564, 566 of quad-phasic pulses 561, 563. For the mono-phasic pulses, the pulse width duration equals the total pulse width of the entire pulse. For the bi-phasic pulses, the pulse width duration values correspond to one half of the total pulse width, as the biphasic pulses used in the study had two equal duration phases, unlike the bi-phasic pulses of the present disclosure that have an initial pulse width an abbreviated pulse width. For the quad-phasic pulse, the first and fourth phases had abbreviated pulse widths relative to the second and third phases. The second and third phases had substantially equal pulse widths, and the first and fourth phases had pulse widths of about one-half the pulse widths of the second and third phases.

As can be seen in graph 600, at relatively long pulse widths in region 602, the different pulses all cause stimulation of heart tissue at relatively similar amplitudes, e.g. between about 500 mV and about 1 V, with the mono-phasic cathodic pulses having the highest amplitude that does not cause simulation. In this region, the pulse widths are between about 250 microseconds to about 500 microseconds.

Beginning in region 604, the amplitudes at which the different pulses cause stimulation of the heart begin to separate. For instance, particularly between pulse lengths of about 75 microseconds and about 50 microseconds there is clear separation in the amplitudes at which the different pulses cause stimulation. As can be seen, both quad-phasic pulses have overtaken the other pulses in terms having the highest amplitudes, which are still not stimulating at pulse widths of about 60 microseconds.

By the time the pulse widths go down to between 25 microseconds or 20 microseconds and 5 microseconds, the differences between the amplitudes required before the quad-phasic pulses cause stimulation and the other pulses cause stimulation is significant. For example, at 6 microseconds, the quad-phasic pulses require around 40 V in order to cause stimulation of the heart, while the bi-phasic pulses only require around 20 V or 22 V. The mono-phasic pulses in this pulse width range require only between 9-11 V to be stimulating.

In some cases, it is contemplated that the electrical stimulation pulses, which are meant to capture the heart, may be delivered using a first polarity, and the communication pulses, which are not meant to capture the heart, may be delivered using a second opposite polarity. For example, in the example LCP 100 shown in FIG. 1, the pulse generator module 104 may deliver electrical stimulation pulses using electrodes 114. In the example shown, electrodes 114 include a smaller electrode on the left end of the LCP 100 and an annular surface electrode toward the right side of the LCP 100. The smaller electrode on the left end of the LCP 100 may have a significantly smaller surface area than the larger annular surface electrode toward the right side of the LCP 100. Thus, when an electrical pulse is delivered between these two electrodes, the current density at the smaller electrode on the left end of the LCP 100 is higher than the current density at the larger annular surface electrode. As such, it is often desirable to place the smaller electrode adjacent or in contact with the heart tissue to reduce the energy required to capture the heart. When so provided, the polarity of the electrical stimulation pulses may be delivered such that the smaller electrode functions as the cathode and the larger annular surface electrode toward the right side of the LCP 100 functions as the anode.

While it is desirable to reduce the energy required to capture the heart (i.e. reduce the capture threshold) when delivering electrical stimulation therapy, it is often desirable to increase the energy required to capture the heart (i.e. increase the capture threshold) when delivering communication pulses. As such, and in some cases, the polarity of the communication pulses may be delivered such that the smaller electrode on the left end of the LCP 100 functions as the anode and the larger annular surface electrode toward the right side of the LCP 100 functions as the cathode. Alternatively, or in addition, the pulse width duration of the communication pulses may be less than the pulse width duration of the electrical stimulation pulses. As shown in FIG. 12, there may be a significant difference between the capture thresholds when applying pulses in an anodic polarity versus a cathodic polarity, especially for monophasic pulses with pulse width durations of less than about 60 microseconds. In some cases, the electrical stimulation pulses may be delivered using a cathodic polarity with a pulse width duration of greater than 60 microseconds, and the communication pulses may be delivered using an anodic polarity with a pulse width duration of less than 60 microseconds. This is just one example.

It is believed that the first phase of the disclosed bi-, tri-, quad-, and other multi-phasic pulses having first phases with abbreviated pulse widths pre-load the tissue (e.g. heart) in an opposite manner to how the second longer phase loads the heart. That is, depending on the polarity of the first phase, the first phase may draw charge to or push charge away from heart cells. This mechanism may be in direct opposition to how the second phase of the pulse causes the charges near the heart cells to act. Accordingly, this pre-loading may allow for longer pulse width durations (e.g. longer pulse widths in subsequent phases of a pulse) or higher amplitudes to be used for communication pulses without fear of accidentally causing unwanted stimulation of the heart or other tissue. Or, the pre-loading may enhance the safety margin with which a system operates when using conducted communication pulses as it increases the amplitudes at which the communication pulses would cause stimulation. Allowing the use of relatively greater energy communication pulses, without causing unwanted tissue stimulation, may enhance the ability of a receiver to receive the communication pulses, and increasing the safety margin of communication pulses with respect to their stimulating amplitude thresholds.

As detailed above, and in some cases, one or both the pulse width and amplitude of the various abbreviated phases and unabbreviated phases in FIGS. 5A-5B, 6A-6D, 9A-9B, 10A-10B and 11A-11B may be set to help control charge accumulation on excitable tissue and thus reduce the likelihood that the unabbreviated phases will stimulate the tissue.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included on any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. An implantable medical device for implantation into a patient, comprising:
   a housing;
   a pulse generation circuit disposed at least partially within the housing;
   a plurality of electrodes electrically coupled to the pulse generation circuit, the plurality of electrodes being exposed external to the housing; and
   a controller operatively coupled to the pulse generation circuit, the controller configured to:
      command the pulse generation circuit to deliver a sub-threshold phasic conducted communication pulse via at least two of the plurality of electrodes;
      wherein the sub-threshold phasic conducted communication pulse comprises a first phase having a first polarity followed by a second phase having an opposite second polarity;
      the second phase having a duration of less than 20 microseconds; and
      the first phase having a duration of between 30 percent and 60 percent of the duration of the second phase.

2. The implantable medical device of claim 1, wherein the first phase has a first phase amplitude, with the absolute value of the first phase amplitude between 1 and 15 volts.

3. The implantable medical device of claim 1, wherein the second phase has a second phase amplitude, with the absolute value of the second phase amplitude between 1 and 15 volts.

4. The implantable medical device of claim 1, wherein the first phase has a first phase amplitude with an absolute value of between 2 and 7 volts, and the second phase has a second phase amplitude with an absolute value of between 2 and 7 volts.

5. The implantable medical device of claim 4, wherein the first phase has a first phase amplitude with an absolute value of between 1 and 4 volts, and the second phase has a second phase amplitude with an absolute value of between 1 and 4 volts.

6. The implantable medical device of claim 1, wherein the second phase has a duration of less than 12 microseconds.

7. The implantable medical device of claim 1, wherein the second phase has a duration of less than 5 microseconds.

8. The implantable medical device of claim 1, wherein the first phase has a duration of between forty percent and sixty percent of the duration of the second phase.

9. The implantable medical device of claim 1, wherein the first phase and the second phase are each substantially a rectangular pulse, a saw tooth pulse, an exponential pulse, a trapezoid pulse, or a stepped pulse.

10. The implantable medical device of claim 1, wherein the implantable medical device is a Leadless Cardiac Pacemaker (LCP).

11. The implantable medical device of claim 1, wherein the implantable medical device is a Subcutaneous Implantable Cardioverter-Defibrillator (SICD).

12. A medical device, comprising:
    a housing;
    a pulse generation circuit disposed at least partially within the housing;
    a plurality of electrodes electrically coupled to the pulse generation circuit, the plurality of electrodes being exposed externally to the housing; and
    a controller operatively coupled to the pulse generation circuit, the controller configured to:
       command the pulse generation circuit to deliver a sub-threshold phasic conducted communication pulse via at least two of the plurality of electrodes;
       wherein the sub-threshold phasic conducted communication pulse comprises at least three phases of alternating polarity including a first phase followed by a second phase followed by a third phase, each having a duration;
       the duration of the second phase of the sub-threshold phasic conducted communication pulse being less than twelve microseconds; and
       the duration of the first phase of the sub-threshold phasic conducted communication pulse being between thirty percent and sixty percent of the duration of the second phase of the sub-threshold phasic conducted communication pulse.

13. The medical device of claim 12, wherein each phase of the sub-threshold phasic conducted communication pulse has an amplitude, and wherein the first phase and the third phase have a first polarity and the second phase has a second opposite polarity.

14. The medical device of claim 13, wherein the duration of the second phase is less than 6 microseconds.

15. The medical device of claim 13, wherein the duration of the first phase of the sub-threshold phasic conducted communication pulse is between 40 percent and 60 percent of the duration of the second phase of the sub-threshold phasic conducted communication pulse.

16. The medical device of claim 13, wherein the duration of the second phase is less than 3 microseconds, and the duration of the first phase is between 40 percent and 60 percent of the duration of the second phase.

17. The medical device of claim 13, wherein the duration of the first phase plus the duration of the third phase is substantially equal to the duration of the second phase so that the sub-threshold phasic conducted communication pulse is substantially charge balanced.

18. The medical device of claim 12, wherein the sub-threshold phasic conducted communication pulse is substantially charge balanced.

19. A method for communicating between devices using conducted communication pulses that pass information through stimulatable tissue in a patient that can be captured, the method comprising:
  deliver a pre-load sub-threshold pulse of a first polarity that preloads the stimulatable tissue with a charge of the first polarity; and
  deliver a conducted communication pulse of a second opposite polarity that would otherwise capture the stimulatable tissue if it were not for the preload of the stimulatable tissue with the charge of the first polarity by the pre-load sub-threshold pulse.

20. The method of claim 19, wherein the conducted communication pulse has a pulse width of less than twelve microseconds, and the pre-load sub-threshold pulse has a pulse width that is thirty to sixty percent of the pulse width of the conducted communication pulse.

* * * * *